United States Patent [19]

Votruba et al.

[11] Patent Number: 5,724,970
[45] Date of Patent: Mar. 10, 1998

[54] MULTIPOSITIONAL MRI FOR KINEMATIC STUDIES OF MOVABLE JOINTS

[75] Inventors: Jan Votruba, Elmont; Rajendra Shenoy, Commack; Raymond V. Damadian, Woodbury, all of N.Y.

[73] Assignee: Fonar Corporation, Melville, N.Y.

[21] Appl. No.: 43,505

[22] Filed: Apr. 6, 1993

[51] Int. Cl.⁶ .................................... A61B 5/055
[52] U.S. Cl. .................. 128/653.2; 128/653.5; 128/781; 5/601; 5/622; 5/624
[58] Field of Search .............. 128/653.1, 653.2, 128/653.5, 882, 781, 774; 5/601, 621–624; 378/208

[56] References Cited

U.S. PATENT DOCUMENTS

| | | | |
|---|---|---|---|
| 4,834,112 | 5/1989 | Machek et al. | 128/777 |
| 4,875,485 | 10/1989 | Matsutani | 128/653.5 |
| 5,054,489 | 10/1991 | Axel et al. | 128/653.2 |
| 5,305,749 | 4/1994 | Li et al. | 128/653.2 |
| 5,305,750 | 4/1994 | Makita . | |
| 5,349,956 | 9/1994 | Bonutti | 128/653.1 |

*Primary Examiner*—Ruth S. Smith
*Attorney, Agent, or Firm*—Brooks Haidt Haffner & Delahunty

[57] ABSTRACT

Methods and apparatus for kinematic studies of the movable joints of the body using magnetic resonance imaging. The apparatus controls the position of movable joints at a multiplicity of predetermined positions, enabling the controlled movement of the joints to each of the predetermined positions. It also includes a device which automatically sequences the movement of a movable joint to each position among the multiplicity of predetermined positions, and the acquisition of magnetic resonance imaging data at each of these positions. These features enhance the clinical utility of kinematic studies of movable joint functionality by magnetic resonance imaging.

71 Claims, 16 Drawing Sheets

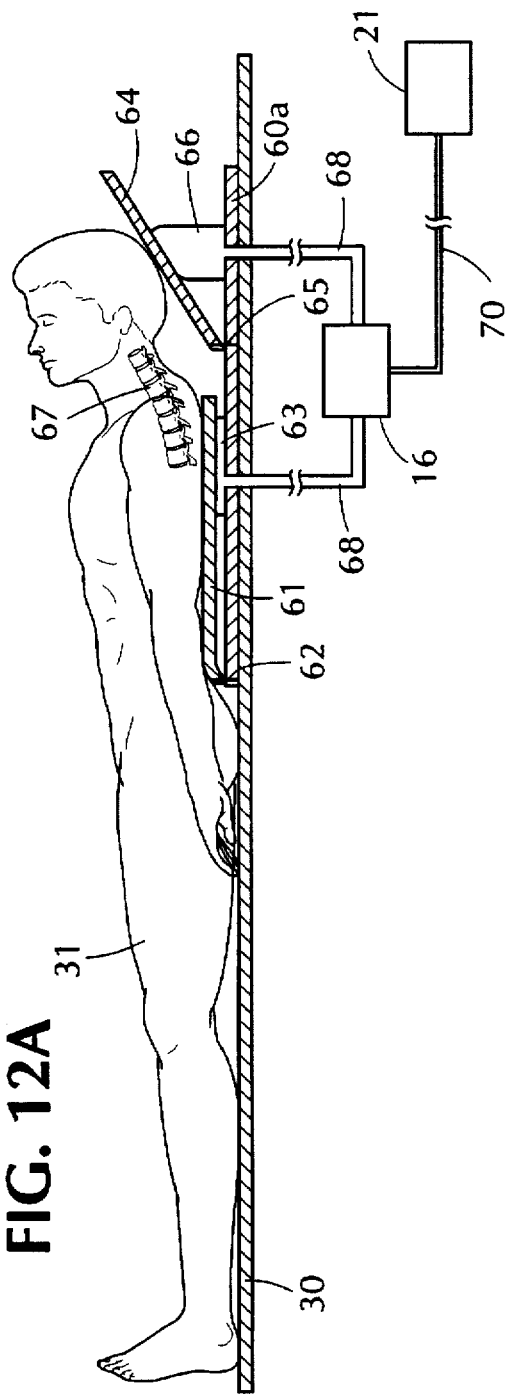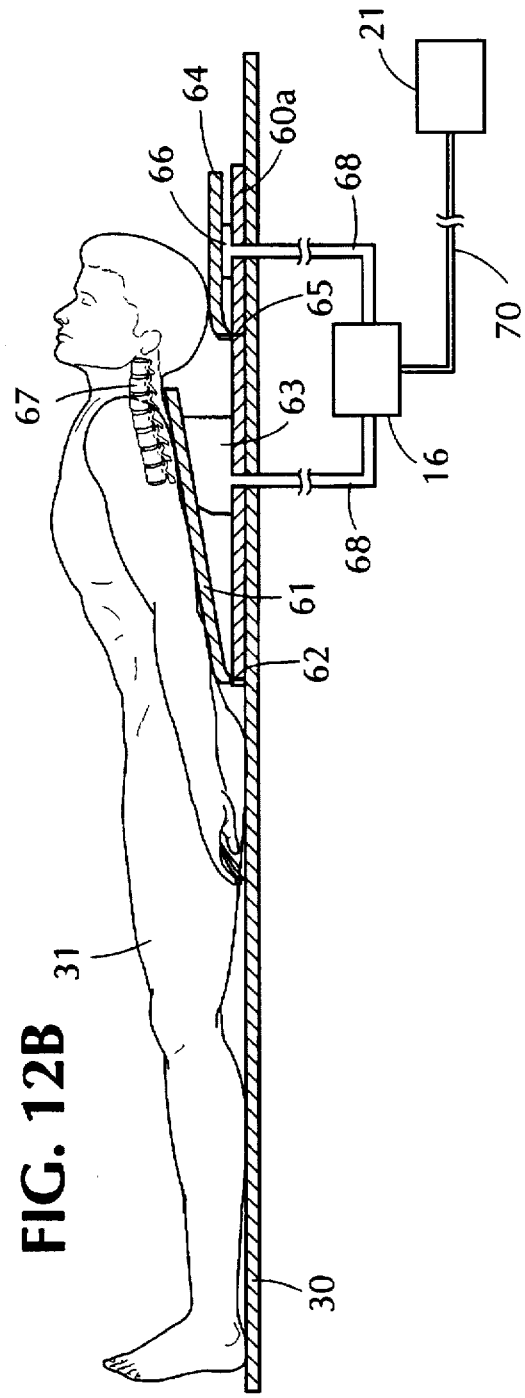

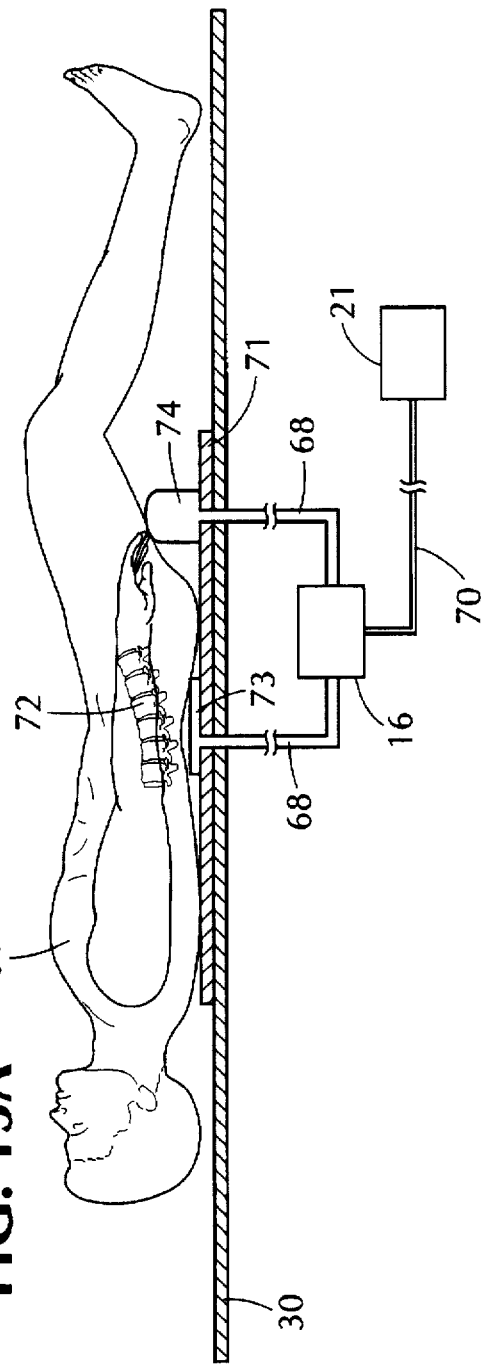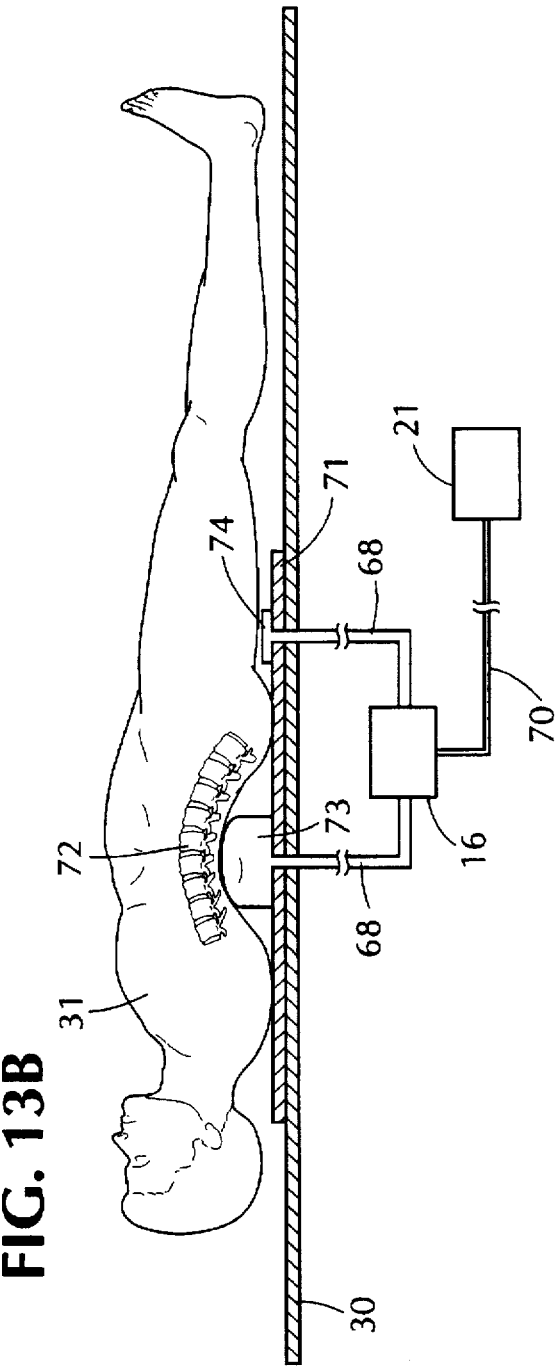

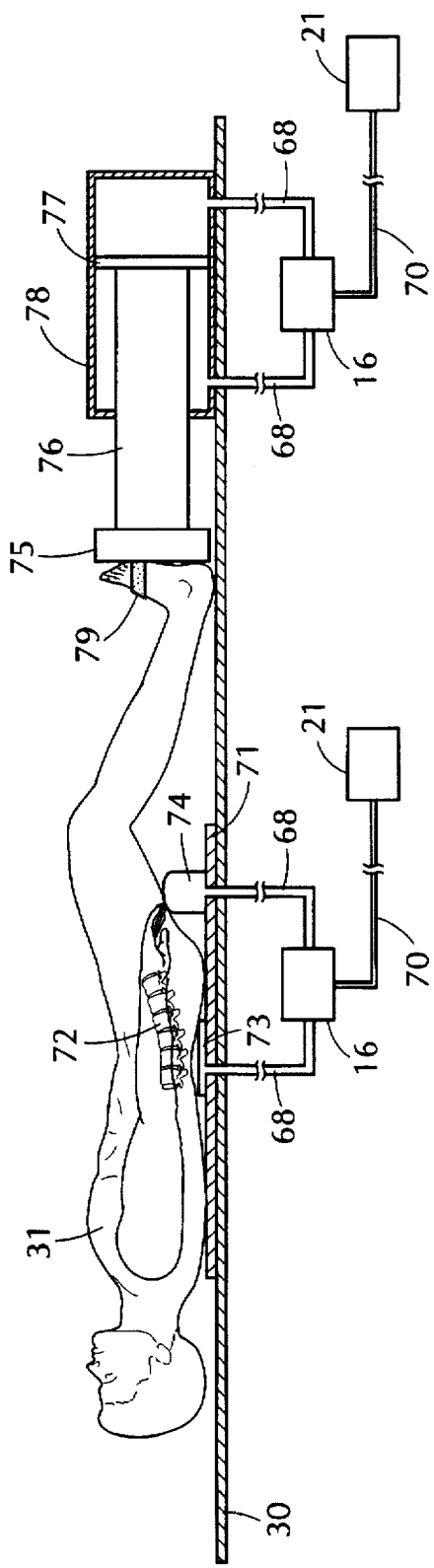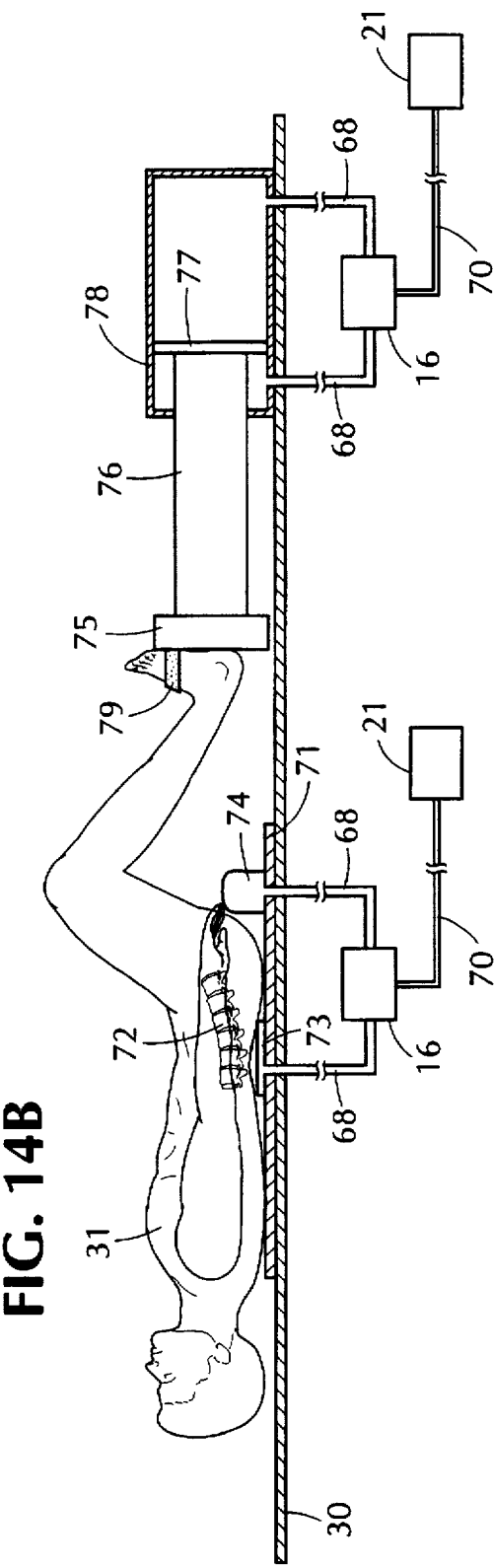

MULTIPOSITIONAL MRI FOR KINEMATIC STUDIES OF MOVABLE JOINTS

BACKGROUND OF THE INVENTION

Magnetic resonance imaging, or MRI, has gained widespread utility for diagnosis as related to the various movable joints of the body, including as examples, the knee, cervical spine and the shoulder. In most instances, magnetic resonance images of the movable joints are made using standard multi-slice pulse sequences. The joint of interest to a particular MRI study is immobilized in a single position, with the various cross-sectional views taken of the joint in one position.

However, important functional information regarding a joint is contained in the "operation" of the joint when it moves through its natural range of motion. In order to make the kinematic study of movable joints practical and of clinical utility, fixtures which interface between the movable joints of a patient and the magnetic resonance imaging apparatus are necessary.

Such fixtures should incorporate a number of important features. For example, fixtures should enable a sufficient range of motion of the joint to provide a complete view of joint functionality. In addition, the fixtures should provide for numerous incremental joint positions over the range of motion, with precise control, to enable a kinematic representation of the joint motion. Furthermore, the movement of the joint among the different positions, and the acquisition of magnetic resonance imaging data at each of these positions should be automated to enhance the practical implementation of multipositional joint imaging. Finally, to provide a high level of clinical utility, the fixtures should accommodate most of the major movable joints of the body.

At the present time only limited studies have been conducted with respect to some of the movable joints of the body, but all these studies are limited by a lack of apparatuses and methods which make the capability of kinematic study of movable joints of the body a common feature of magnetic resonance imaging apparatuses. Thus useful diagnostic information obtained in a standard clinical setting has not been achieved.

Current techniques for kinematic joint studies are generally characterized by a small number of positions of the joint; a small range of motion of the joint; manual operation of the apparatus in a cumbersome fashion; and failure to address comprehensively the various joints of the body, and the different directions of motion any given joint may be capable of.

The object of the invention described herein is to provide a new and useful dimension to the clinical utility of magnetic resonance imaging as related to multipositional studies of the movable joints of the body.

SUMMARY OF THE INVENTION

A number of fixtures are described herein which enable the multipositional imaging of movable joints of the body thus making kinematic studies a practical technique to be employed clinically in medical diagnostic imaging.

One fixture described herein features a rotatable plate which is used to locate and immobilize a portion of anatomy on one side, typically the inferior side, of a movable joint. A portion of anatomy on the other side of, or superior to, the movable joint will be immobilized on a stationary part of the apparatus. The portion of anatomy which is attached to the rotatable plate will undergo movement concurrently with the movement of the rotatable plate. The position of the rotatable plate is incrementally moved resulting in a multiplicity of positions of the movable joint. At each position magnetic resonance imaging data are acquired.

In another embodiment, inflatable and deflatable air bags separated by some distance, are used to control the extent of flexion and extension of a region of the spine. For example, in studies of the cervical spine, one air bag is placed beneath the head, and a second air bag is placed beneath the shoulders of a patient. By transferring air between the air bags, in a series of steps, a multiplicity of positions of the cervical spine ranging from flexion to extension is generated. Magnetic resonance imaging data are collected at each of the multiplicity of positions.

Another fixture is employed to obtain multipositional magnetic resonance images of the temporomandibular joint (TMJ). Here the head and the upper jaw of a patient are immobilized and the lower jaw is moved by means of a bite at the end of a movable rod. The position of the TMJ is changed in a series of steps by changing the position of the movable rod.

Another embodiment of the present invention is an apparatus and method for the efficient and automatic sequencing of joint movement and magnetic resonance imaging. This is achieved through use of a programmable control unit which interfaces with both the magnetic resonance imaging apparatus which executes the imaging study, and with the driving force that changes the position of the movable portion of each fixture, and thus the movable joint.

In different embodiments, a fixture is either mounted on the patient bed beneath the patient where access to the imaging volume is achieved by positioning the bed centrally in the magnet gap, or separately mounted in the imaging volume in which case the bed with the patient is positioned in the magnet gap off-center, either to the left or to the right of the imaging volume. The off-center patient loading into the magnet gap is a novel aspect of this invention.

The precise control of the position of the movable joints of a patient, and the automatic sequencing of joint movement and imaging data acquisition make kinematic imaging of joint movement a useful clinical tool for the study of joint functionality.

3

Figure 10:
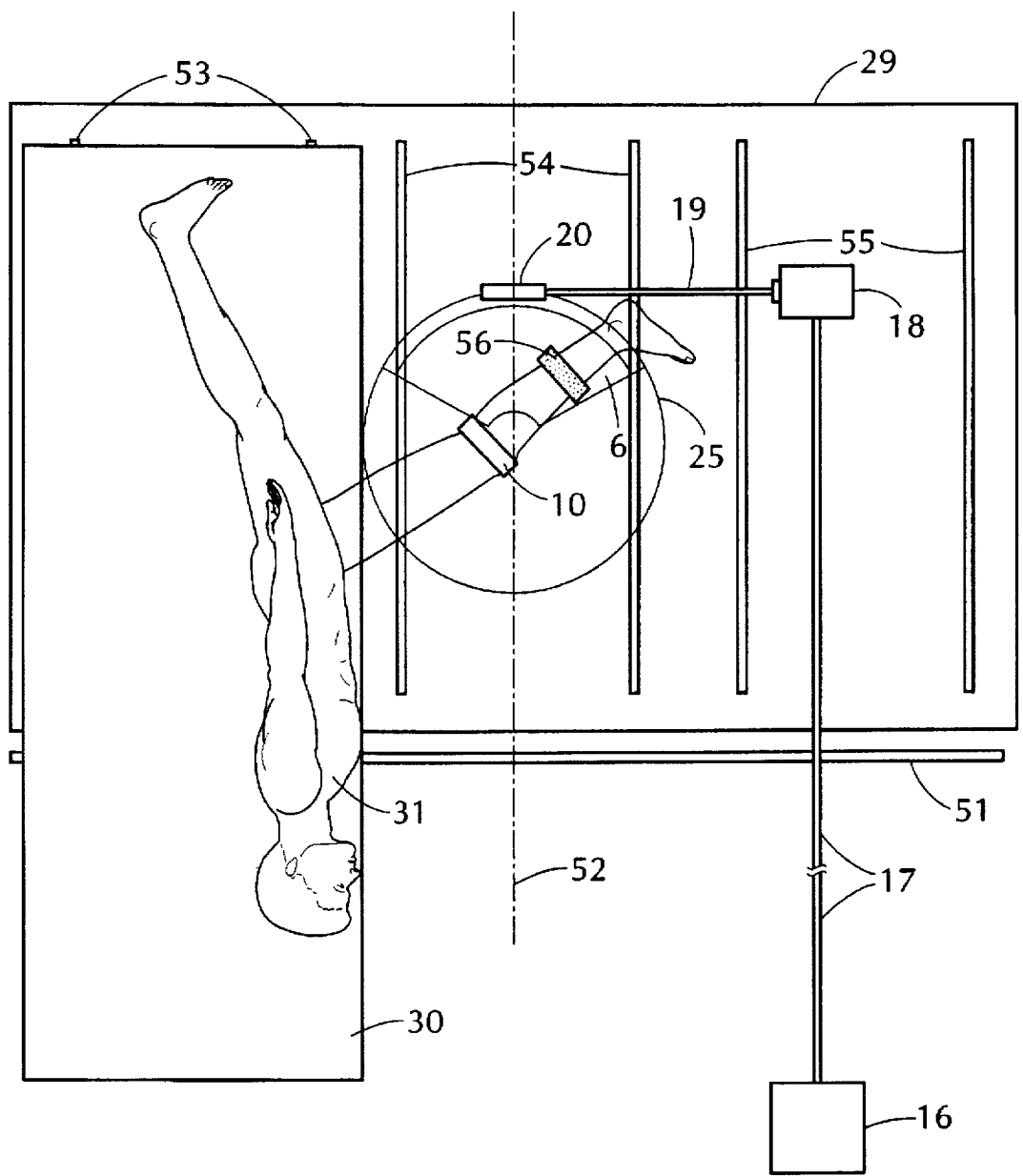

FIG. 10 Plan view from inside the magnet gap of a patient with the knee extended and positioned for multipositional magnetic resonance imaging of the knee.

Figure 11:
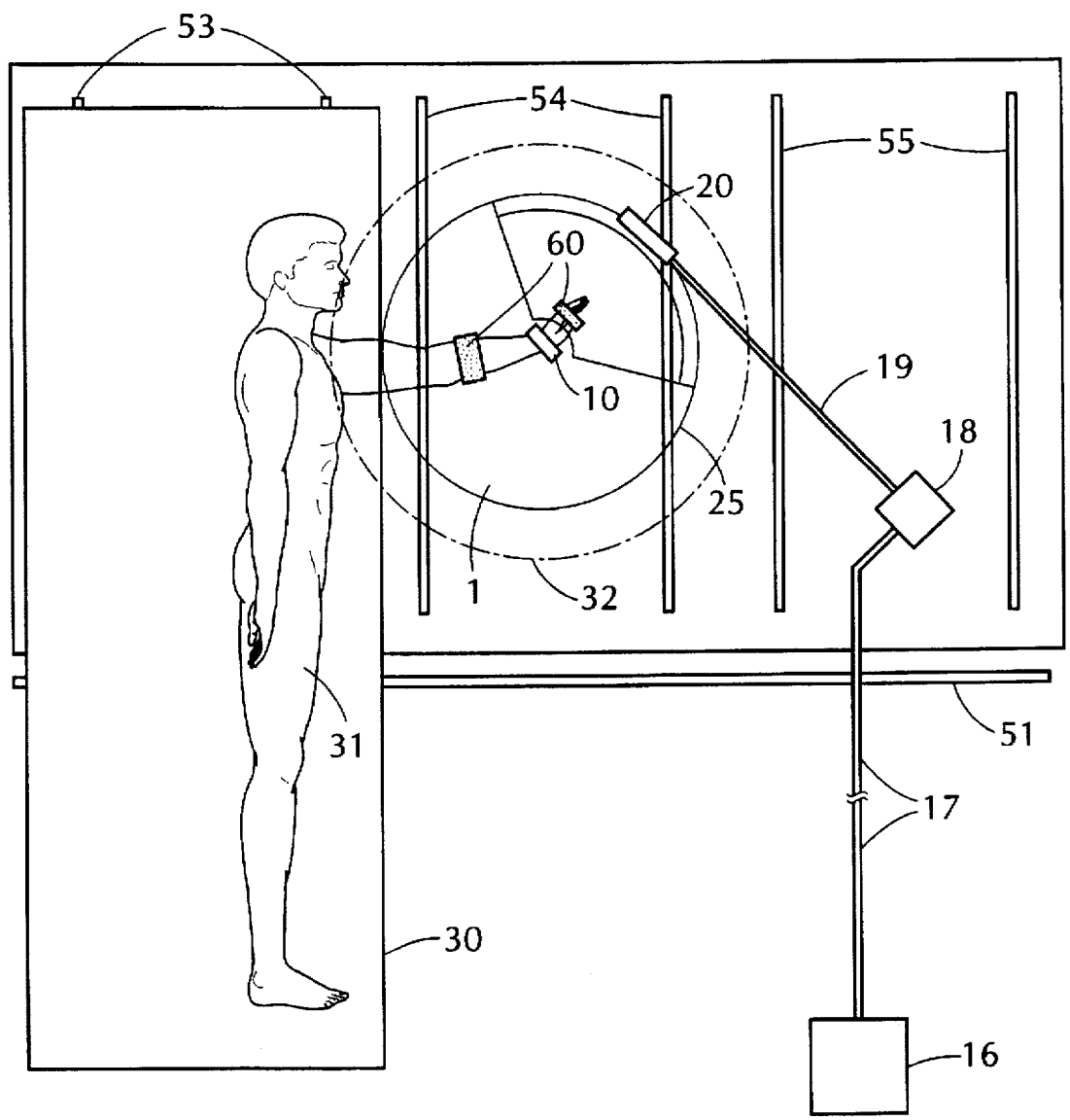

FIG. 11 Plan view from inside the magnet gap of a patient positioned for multipositional magnetic resonance imaging of the wrist.

FIG. 12a Lateral view of a patient positioned for multipositional magnetic resonance imaging of the cervical spine, with the cervical spine flexed.

FIG. 12b Lateral view of a patient positioned for multipositional magnetic resonance imaging of the cervical spine, with a cervical spine extended.

FIG. 13a Lateral view of a patient positioned for multipositional magnetic resonance imaging of the lumbar spine, with the lumbar spine flexed.

FIG. 13b Lateral view of a patient positioned for multipositional magnetic resonance imaging of the lumbar spine, with the lumbar spine extended.

FIG. 14a Lateral view of patient positioned for multipositional magnetic resonance imaging of the lumbar spine, with the lumbar spine flexed.

FIG. 14b Lateral view of patient positioned for multipositional magnetic resonance imaging of the lumbar spine, with flexion aided by piston accessory.

Figure 15:
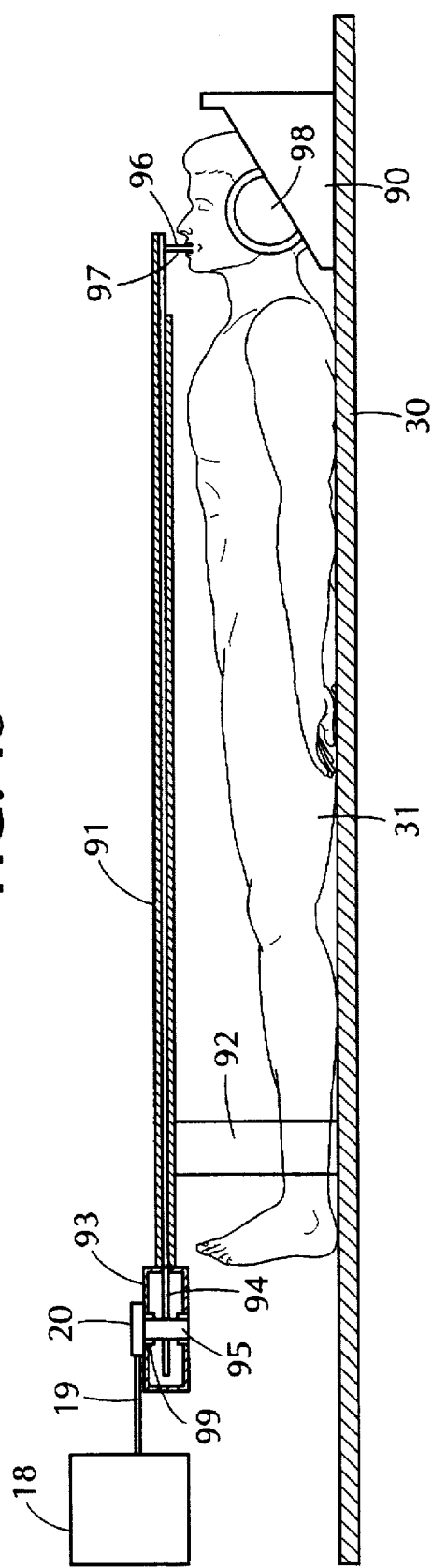

FIG. 15 Lateral view of a patient positioned for multipositional magnetic resonance imaging of the temperomandibular joint.

Figure 16:
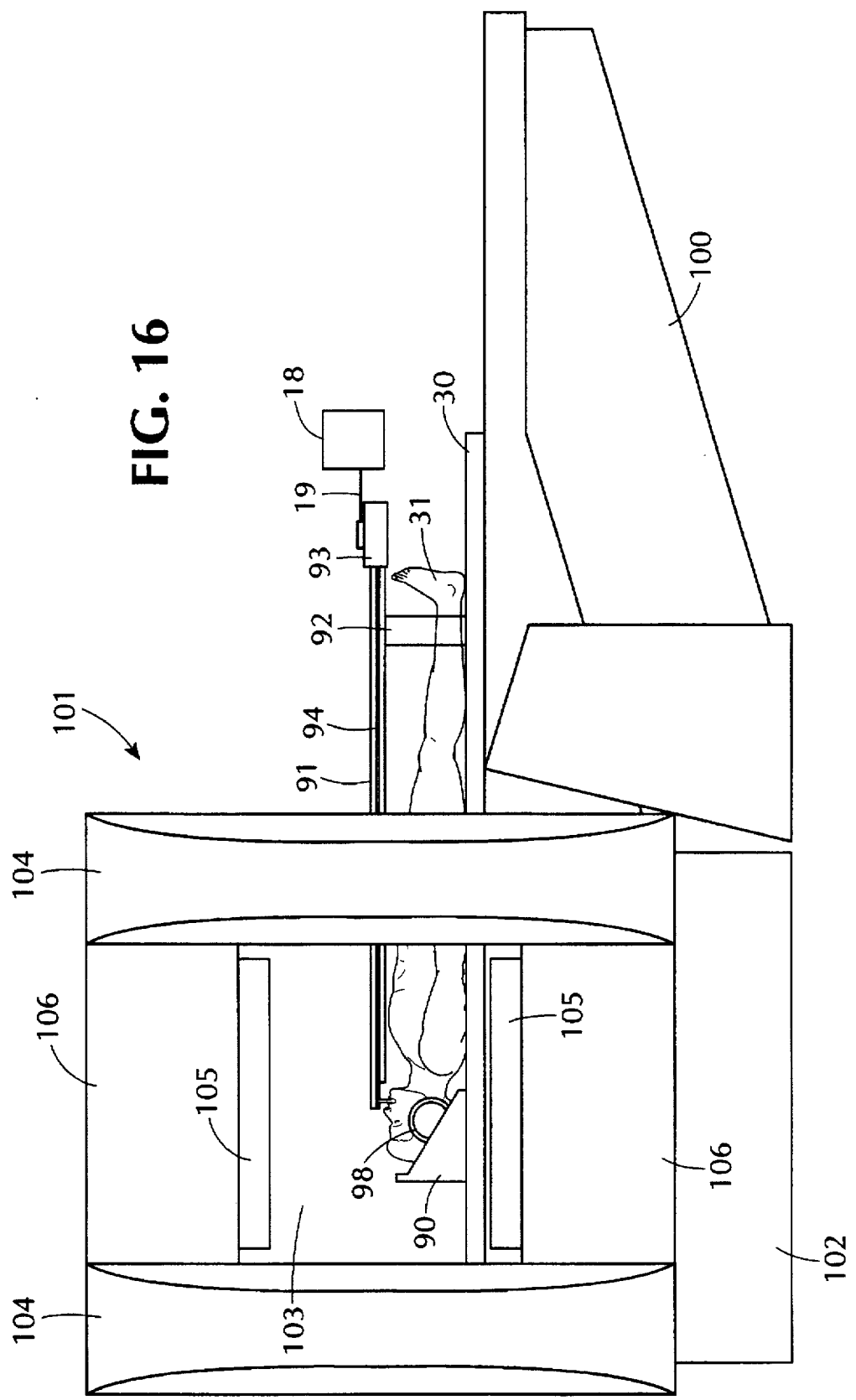

FIG. 16 Lateral view of a patient in a multiple access primary field magnet, positioned for multipositional imaging of the temperomandibular joint.

DETAILED DESCRIPTION OF THE PREFERRED EMBODIMENTS

The present invention pertains to fixtures designed to incrementally control the movement, and the position of the movable joints of a patient. The precise positioning of the movable joints of the body, with such fixtures enables the careful evaluation of joint functionality, by means of kinematic studies employing a series of magnetic resonance images.

Modern day magnetic resonance imaging apparatus share several common features which arise from the basic requirements of the imaging technique and the need to interface with the patient in a practical manner.

The MRI apparatus has a primary field magnet which provides a static background field typically in the range from 600 gauss to 40,000 gauss. Such magnetic field levels provide the necessary signal-to-noise for imaging. Primary field magnets are categorized according to the source of magnetic energy and are of three standard types, namely, permanent magnets, resistive electromagnets, and superconductive electromagnets. Commonly assigned U.S. Pat. Nos. 4,707,663, 4,675,609, and 4,766,378 introduced the iron core structure into MRI primary field magnet design. Prior to these inventions, MRI magnets were generally of the air-core design and lacked the benefits of iron. For this description, we define primary field magnets as inclusive of both air-core magnets and iron-core magnets as originally introduced by the above inventions (commonly assigned U.S. Pat. Nos. 4,707,663, 4,675,609, and 4,766,378). Moreover, both resistive and superconductive magnets are electromagnets.

The primary field magnet has a magnet gap which is an opening large enough to accommodate a patient; and also an imaging volume, representing a smaller portion of the magnet gap which has the proper attributes for actually conducting the MRI study. More specifically, the imaging volume will have a highly uniform magnetic field, pulsed magnetic field gradients and radio frequency antennas. In addition the MRI apparatus includes a patient handling system, part of which is a movable patient bed that transports the patient into and out of the magnet gap, and positions the patient in the imaging volume.

Figure 1:
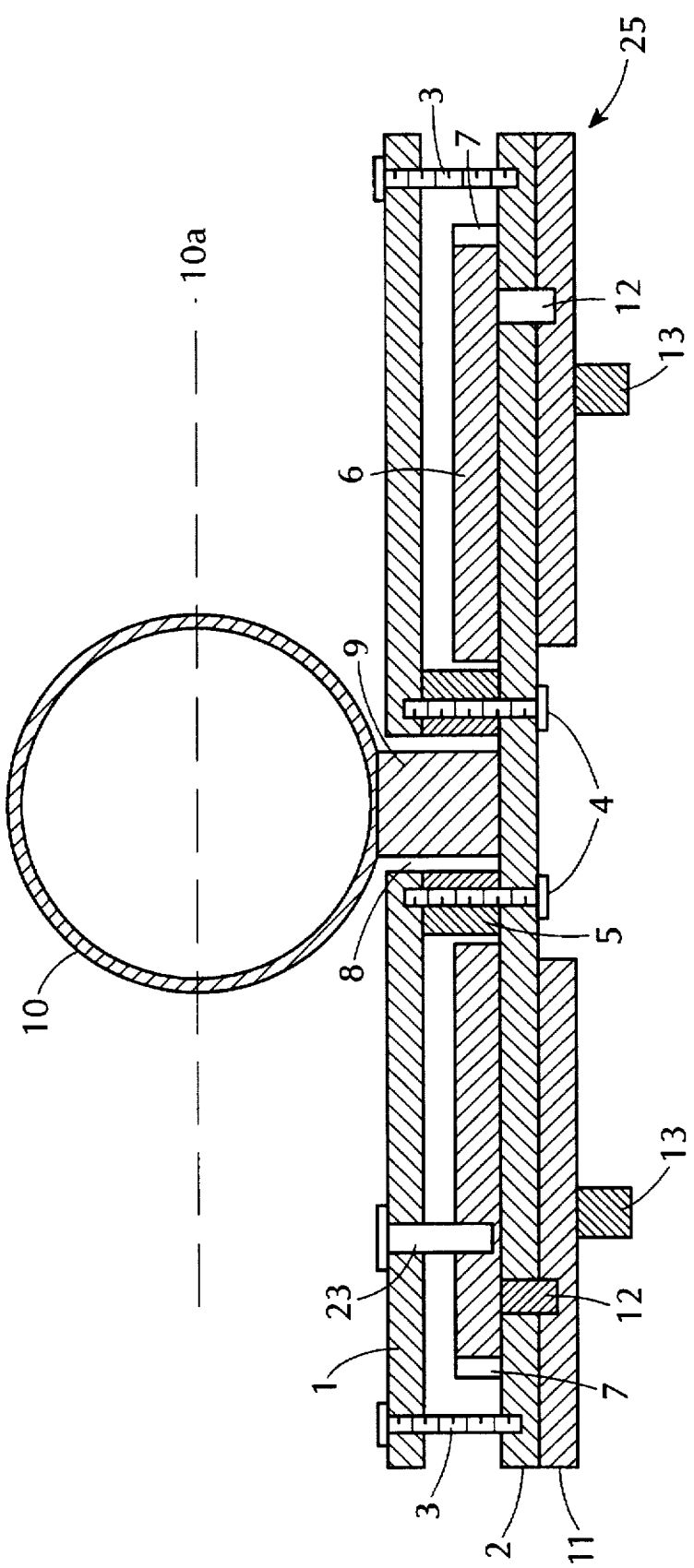
FIG. 1 Cross-sectional view of the turntable assembly.
Figure 2:
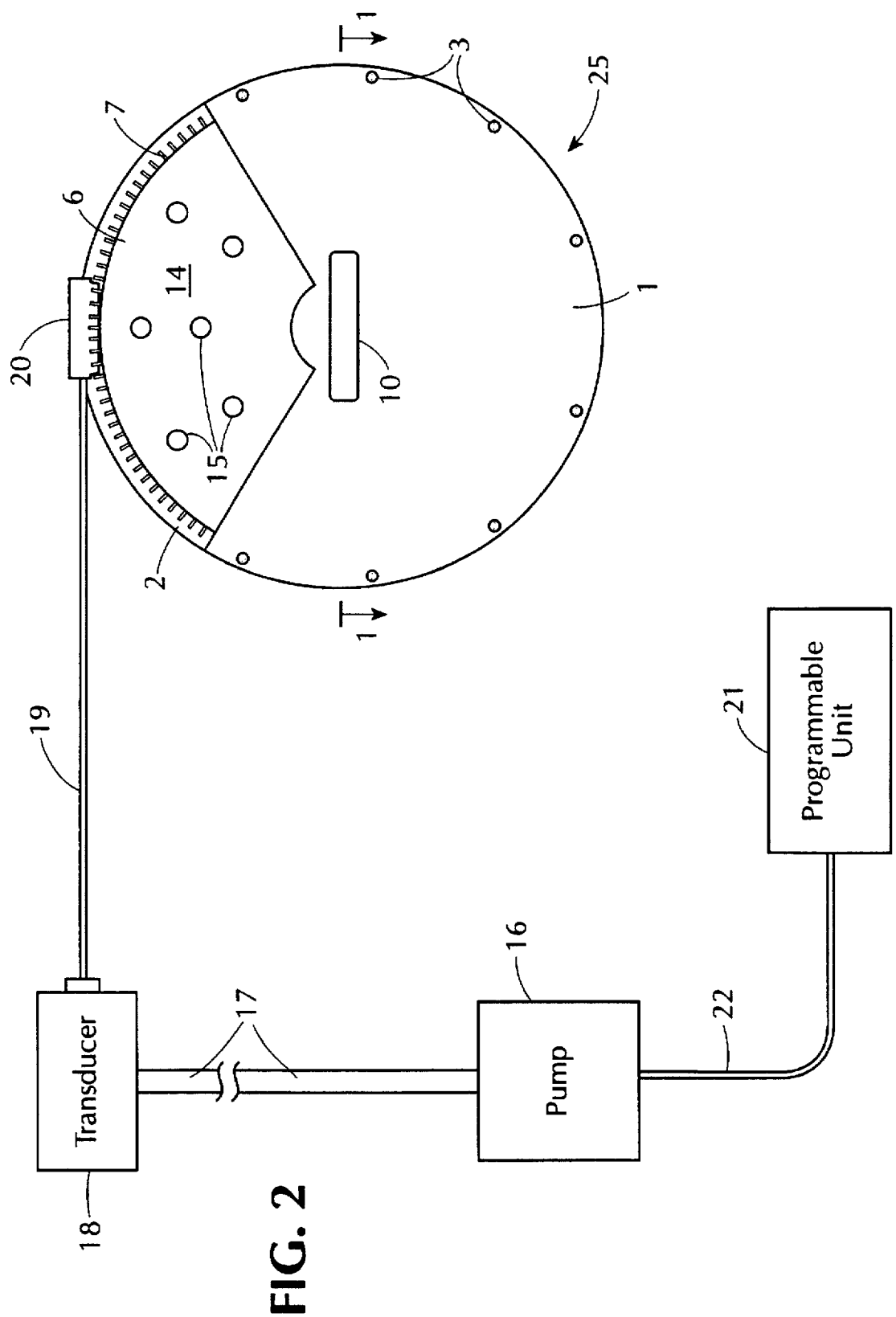
FIG. 2 Plan view of the turntable assembly with transducer, peristaltic pump and programmable unit.

Many of the movable joints of the body exhibit rotational motion, with the movable joint being the origin of such rotation. The present invention includes a turntable assembly, part of which is designed to move in a rotational fashion. FIG. 1 is the preferred embodiment of such a turntable assembly 25, and represents a vertical section at the section line 1—1 as shown in FIG. 2. Shown is a top plate 1 attached to a bottom plate 2, with fasteners 3, placed around the periphery of the turntable assembly 25, and fasteners 4, near the center of the turntable assembly 25. The central fasteners 4, secure the top and bottom plates together through an intervening collar 5. The middle or rotatable plate 6, rests on the lower plate 2, is of slightly smaller diameter than the top plate 1 and bottom plate 2, and is free to rotate. The rotatable plate 6, contains a central hole which is large enough to surround the collar 5. The fit of the rotatable plate around the collar 5 is tight enough to minimize or eliminate lateral motion of the rotatable plate 6, relative to the collar 5, but loose enough to allow free rotational motion. There is provision for the placement of a removable locking pin 23, which passes through a hole in the upper plate 1, and captures one of the threaded holes 15, in the rotatable plate 6. The rotatable plate 6 is restrained from moving when the locking pin 23 is employed.

The circumference of the rotatable plate 6, contains teeth 7, which may be machined as an integral feature of the rotatable plate structure, or alternatively, added to the circumference in the form of a belt with a flat surface on one side for attachment to the edge of the rotatable plate, and a tooth pattern on the other side of the belt. Engagement of the teeth 7, on the circumference of rotatable plate 6, allows the application of force by an external means to rotate and position the rotatable plate 6. It is the rotatable plate 6, to which various anatomical regions of a patient will be attached in order to effect joint movements.

Alternative means for transferring an external force to a location on the circumference of the middle plate are also within the scope of this invention. As an example, a high friction, non-slip contact strip could be used in place of teeth.

Into the central hole 8, in the turntable assembly 25, can be placed a cylindrical post 9, to which is attached a radio frequency antenna 10, for use during magnetic resonance imaging studies. The post 9 and associated antenna 10 rest on the lower plate 2 and are free to rotate as a unit inside the central hole 8.

The anatomical joint of interest is generally placed into the aperture of the radio frequency antenna 10, and as the joint moves through its particular range of motion, the ability of the radio frequency antenna 10 to freely rotate accommodates the multiplicity of positions of the joint. This rotatability of the radio frequency antenna 10 will permit a constant spatial relationship between the radio frequency antenna 10 and the anatomical joint of interest to be maintained. Such an arrangement is advantageous since it avoids artifactual changes in illumination in the magnetic resonance images due to changes in the spatial relationship between the joint and the antenna as the joint moves through an arc of rotation. Furthermore, the range of motion of the joint will not be limited due to mechanical obstruction as might occur in the case of a stationary antenna.

Depending upon the particular joint being imaged, radio frequency antennas of different size and shape may be used to insure optimal performance. For example, a radio frequency antenna which yields optimal performance when imaging the shoulder would be less preferable when generating images of the ankle where a smaller diameter antenna providing better filling factor would be chosen. Thus, the use of different radio frequency antennas is within the scope of this invention. Furthermore, a radio frequency antenna 10 may function as a receiver, transmitter, or as a duplex antenna for transmitting and receiving radio frequency data. Radio frequency antennas are changed by removing the antenna 10 and associated post 9 from the central hole 8, and inserting a different antenna and associated post into the central hole 8.

The turntable assembly 25 is mountable on a carriage 11, by means of a series of alignment pins 12 which are permanently attached to the bottom plate 2 and securely fit into holes in the carriage 11. The carriage 11, contains two tracks 13, designed to travel on a set of tracks 54 (see FIG. 9) positioned in the magnet gap. The set of tracks 54 also accommodate the travel of the patient bed into and out of the magnet gap. Movement of the carriage 11 on the set of tracks allows the positioning of the turntable assembly 25, in the magnet gap. The vertical positioning of the radio frequency antenna 10 is performed to insure that the center of the RF antenna is coincident with the vertical center of the gap as indicated by the dashed line 10a. This can be accomplished by the appropriate choice of height of the tracks 13, on the carriage 11.

A plan view of the turntable assembly 25 in FIG. 2, reveals additional features of this invention. Unlike the rotatable plate 6, and the bottom plate 2, the top plate 1 is partially cut away to expose a substantial arc portion of the rotatable plate 6. In the preferred embodiment, the exposed arc is approximately 120°. The top surface of the rotatable plate 6 is covered with a velcro-type material 14, to allow the skid-proof placement of accessories which will secure various portions of anatomy to the rotatable plate 6, during motion of the joint. Such accessories may be as simple as straps or as complex as molded restraints as in the case of lateral motion of the cervical spine. The nature of these accessories will become apparent as embodiments employing the turntable assembly are described further below.

An additional feature related to the rotatable plate 6, is a plurality of holes 15, which are typically threaded, and which are used to secure certain other accessories, as required, during magnetic resonance imaging of certain joints. The holes 15, are positioned periodically over the surface of the rotatable plate 6, facilitating easy access regardless of the rotational position of the rotatable plate 6.

Figure 3:
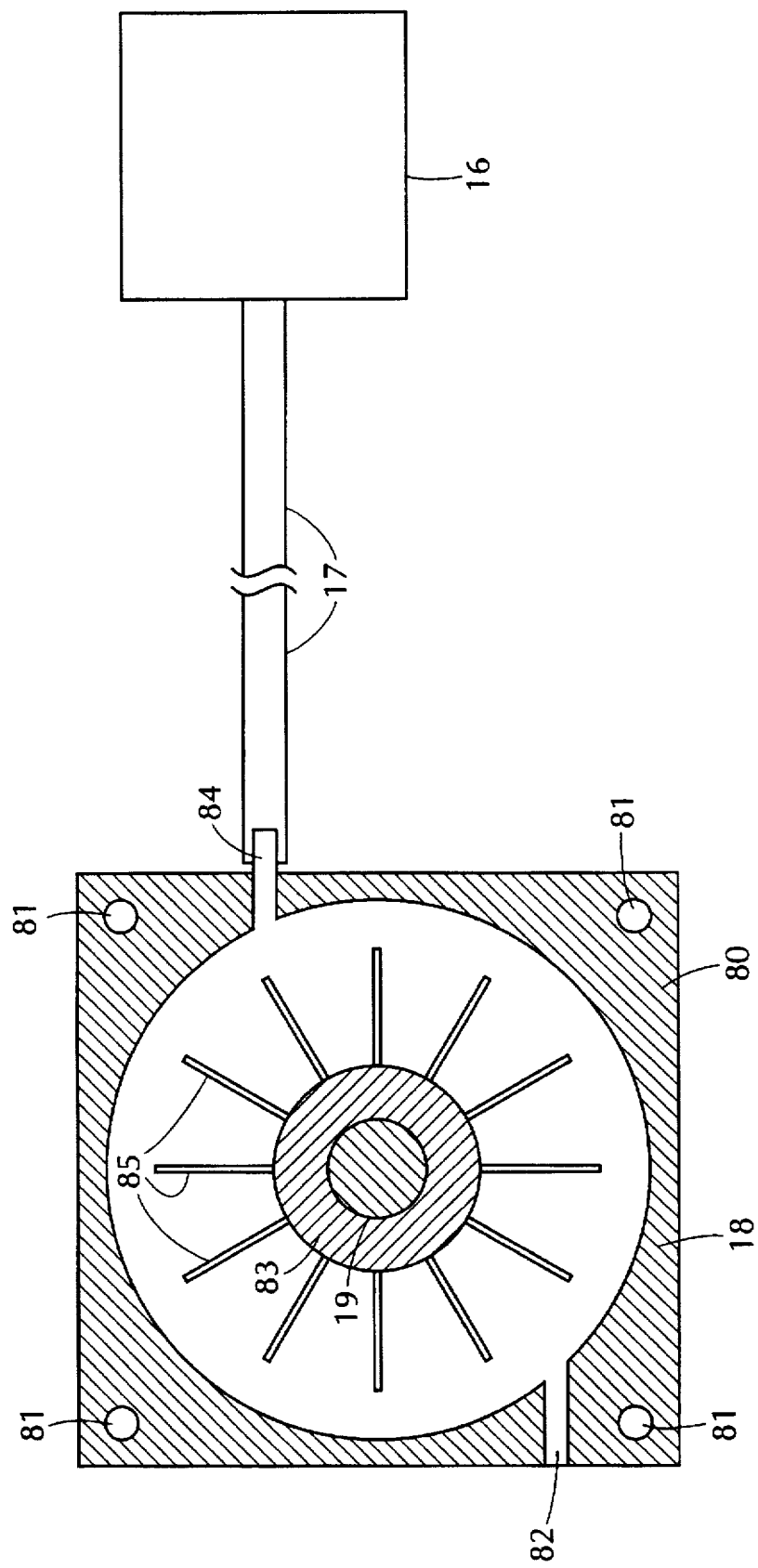
FIG. 3 Cross-sectional view of the transducer.

Also shown in FIG. 2 is the source of the driving force 16, which, in the preferred embodiment, is a peristaltic pump capable of being located at some distance from the primary field magnet. The driving force is transferred pneumatically by means of interconnecting tubing 17, to a transducer 18. The transducer 18, in the preferred embodiment is non-ferromagnetic and thus capable of being positioned in close proximity to, or even inside the primary field magnet. FIG. 3 is a cross-sectional view of the transducer 18, showing a screw hole 81, in each corner of the transducer housing 80 for attachment of a cover plate which supports, and permits free rotation of one end of the rigid rod 19. The opposite end of the transducer housing 80 also has screw holes to secure another cover plate, having a central clearance hole to allow passage of the length of rigid rod 19 through it, as depicted in FIG. 2. All seams of the transducer possess air tight seals, but there is an exhaust port 82 for the release of air pressure. The rigid rod 19 is secured to a finned-structure 83.

In operation, controlled amounts of air from the peristaltic pump 16 are conducted via the tubing 17 through the input nozzle 84 of the transducer 18, and impinge on the fins 85, causing rotation of the finned-structure and rigid rod 19 together. The driving force from the peristaltic pump 16 which is transferred to the transducer 18, is thus converted to mechanical force, and transmitted via a rigid or semi-rigid rod to a gear head 20. The gear head 20, engages the teeth 7 on the circumference of the rotatable plate 6, so that the rotatable plate 6 incrementally changes angular position when the gear head 20 rotates.

Figure 4A:
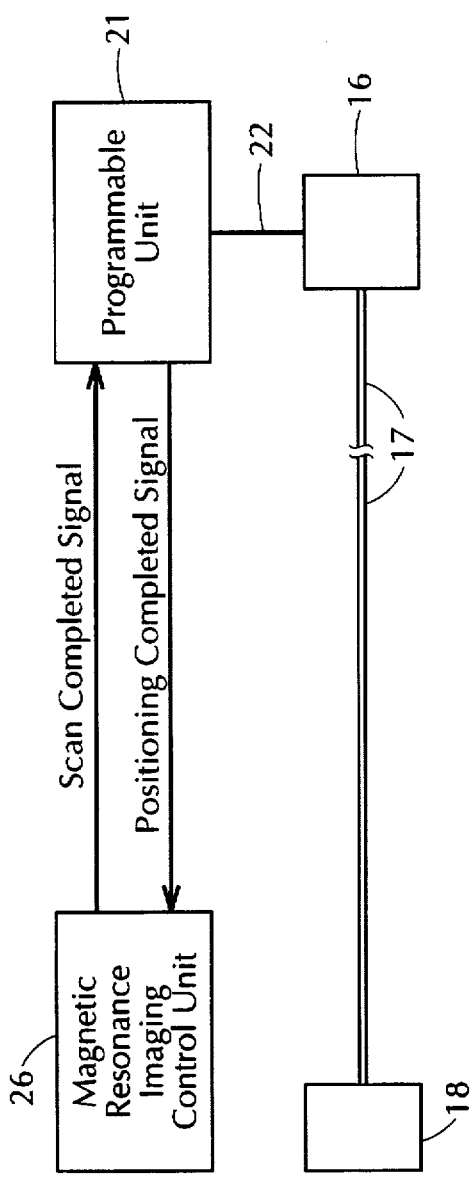
FIGS. 4a and 4b Block diagram and event chronology of the automatic sequence.
Figure 4B:
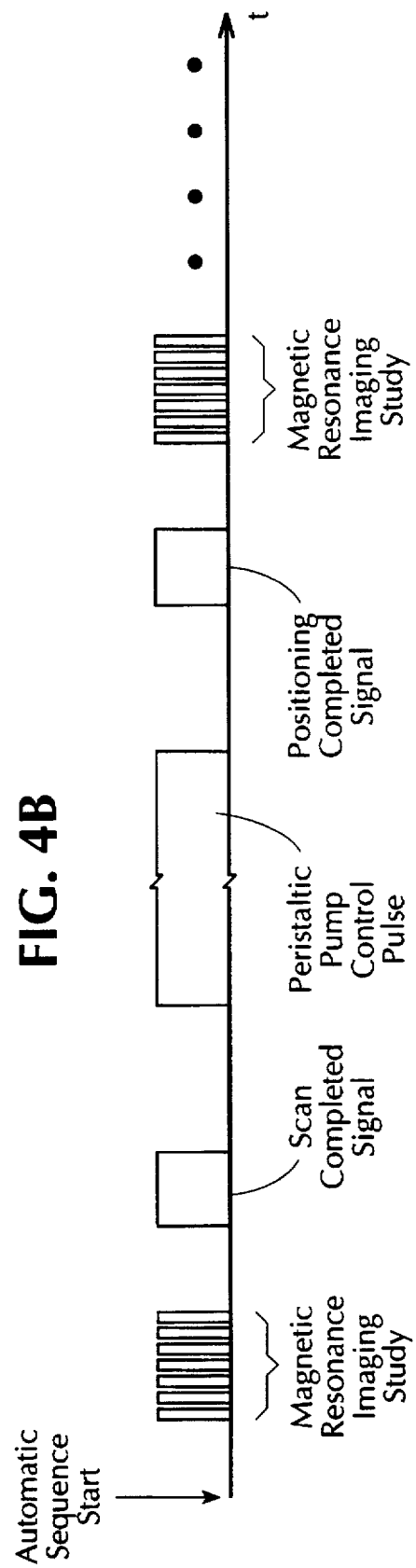

An important feature of this invention is the provision for a computer interface to the peristaltic pump. As depicted in FIG. 2, a programmable unit 21 is connected to the peristaltic pump 16, through interconnecting cables 22. The programmable unit 21, controls various parameters of the movement of the joint through control of the peristaltic pump. For example, parameters such as the size of the rotational angle increment between the multiplicity of fixed positions of the joint at which magnetic resonance imaging data are collected; the number of rotational angle increments; and the full extent of the arc to be traversed for a complete study. In addition, as shown in FIGS. 4a, and 4b the programmable unit 21 is capable of automatically sequencing the movement of a particular joint from an original position to a new position, followed by the automatic initiation of a magnetic resonance imaging study at the new position. This is accomplished through an interface with the magnetic resonance imaging control unit 26.

Following the automatic sequence initiation, a magnetic resonance imaging study is started at a particular position of the movable joint. The imaging study may comprise any number of individual slices. When the imaging study is completed, a scan completed signal is sent to the programmable unit 21, which then initiates operation of the peristaltic pump 16 through a control pulse. The control pulse width varies depending upon the step size of the joint movement where longer control pulses are proportional to larger step sizes. After movement of the joint to a new position is completed, the programmable unit sends a positioning completed signal to the magnetic resonance imaging control unit 26, which initiate another magnetic resonance imaging study at the new position of the movable joint. Automatic sequencing continues until the full complement of joint positions has been imaged.

In the preferred embodiment, the automatic sequencing of imaging at predetermined positions along an arc of rotation and advances in the position of the joint, is carried out as shown in FIGS. 4A and 4b. However, an alternative embodiment in which the host computer of a magnetic resonance imaging apparatus performs the functions of the programmable unit and the magnetic resonance imaging control unit is possible, and is a practice of this invention. In another alternative embodiment where the gear head mechanism used to apply the driving force to the rotable plate is replaced with a ratchet type mechanism it is not necessary to vary the width of the control pulse to change the step size. In this case, the step size is determined by a series of constant-width control pulses. Such pulses are more consistent with a ratchet-type action.

Additionally, alternative embodiments to this invention include the use of hydraulic, electrical or mechanical means instead of pneumatic means to transfer the driving force to the transducer 18. The means utilized to transfer force from the transducer 18, to the rotatable plate 6, may also be hydraulic, pneumatic, or electrical in place of the mechanical means described in the preferred embodiment. Furthermore a ferromagnetic transducer may be used in place of the non-ferromagnetic transducer in instances when the transducer is located at a distance from the imaging volume so that its presence will not affect the diagnostic quality of the images produced.

The apparatus described in FIGS. 1 through FIG. 4 can be broadly utilized to automatically index the motion of several of the movable joints of a patient and provide a magnetic resonance imaging apparatus with the capability to obtain a series of images where consecutive images show the motion of the joint at a multiplicity of positions through an arc of rotation. As used herein, movable joints of the body include, but are not limited to, the knee, shoulder, ankle, elbow, hip, wrist, cervical spine, thoracic spine, lumbar spine, and temporomandibular. Examples of implementation of the turntable assembly 25 to facilitate the acquisition of a series of images at different positions along an arc of rotation for different movable joints will now be described.

The general approach to implementation of the turntable assembly 25, involves attachment of an anatomical region of a patient which is on one side of the movable joint of interest to a stationary part of the magnetic resonance imaging apparatus, and attachment of an anatomical region of the patient which is on the other side of the movable joint, to the rotatable plate 6, or some accessory attached to the rotatable plate 6, of the turntable assembly 25. By so doing, rotational motion of the rotatable plate 6 as detailed herein enables motion of the movable joint.

Figure 5:
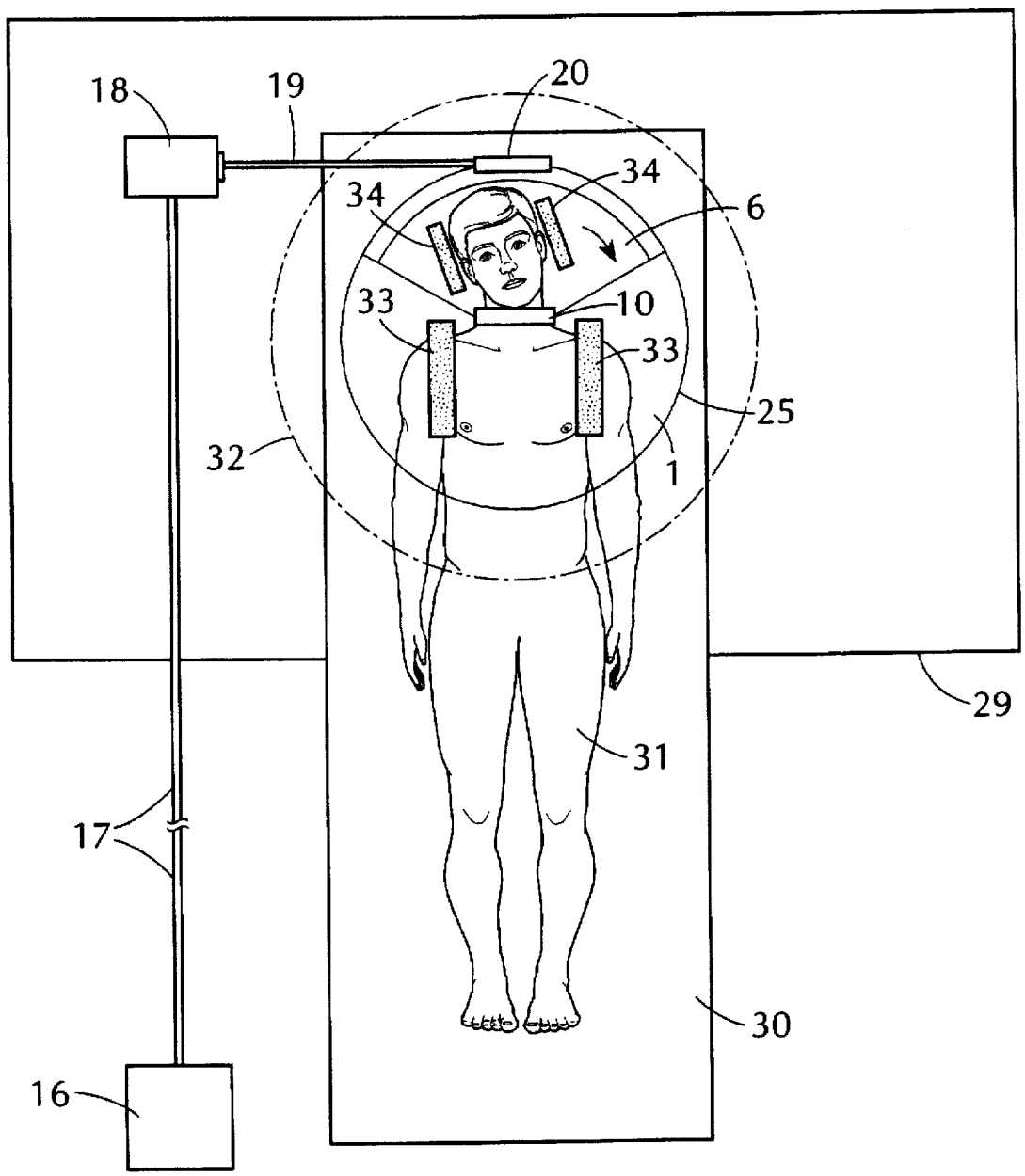
FIG. 5 Plain view from inside the magnet gap of a patient positioned for multipositional magnetic resonance imaging of lateral motion of the cervical spine.

The first illustration of this general approach to implementation of the turntable assembly 25, is in FIG. 5, which shows a plan view of the magnet gap area between the two poles of a magnet, into which a patient is positioned for magnetic resonance imaging. These features are shown relative to a footprint 29, of the primary field magnet structure. The turntable assembly 25, is positioned on the patient bed 30, which is used to move the patient 31 into and out of the imaging volume 32. In order to image a multiplicity of positions generated by lateral motion of the cervical spine, the patient is positioned with the neck in the imaging volume 32, and with the radio frequency receiving antenna 10, positioned around the neck of the patient. Ideally the movable joint of interest is placed as closely as possible to the center of rotation of the rotatable plate 6. Positioning straps 33, secure the upper torso at the position of the shoulder and immobilize the patient inferior to cervical spine. This portion of the patient will remain stationary during the imaging procedure. A head restraint 34, immobilizes the head relative to the rotatable plate 6.

FIG. 5 shows the head laterally maximally displaced to the left side, representing a starting position for the flexure of the cervical spine in this direction. Application of a rotational force at the gear head 20, through the means as described above, rotates the head in a direction indicated by the arrow, toward the opposite or right side maximal lateral position in a series of steps. This motion progressively reduces the degree of flexure of the cervical spine from the left maximal position, through the centered position which has no net lateral flexure, and ultimately to the right maximal lateral flexure position, on the opposite end of the prescribed rotational arc. At a multiplicity of positions along the arc, magnetic resonance imaging takes place, generating a series of progressively positioned images from which a kinematic presentation showing the lateral kinematic motion of the cervical spine may be generated. This is the preferred embodiment of this invention for lateral movement of the cervical spine.

There are alternative embodiments to this invention. For example, alternative means for structural elements 33 and 34 may be used for immobilization. Also the order of the various positions of lateral flexure of the cervical spine need not continuously progress from one extreme position to the other, but may in fact begin at any position and proceed in random order as determined by the programmable unit.

It should be clear that the description of FIG. 5 also applies to generating a series of magnetic resonance images during lateral motion of the ankle. In this later case, the patient is positioned in the imaging volume feet first instead of head first as depicted in FIG. 5. Also, the immobilizing accessories would attach above and below the ankle joint. Rotational motion of the rotatable plate 6, and the acquisition of magnetic resonance images would otherwise be the same as already described for the lateral cervical spine motion.

Figure 6:
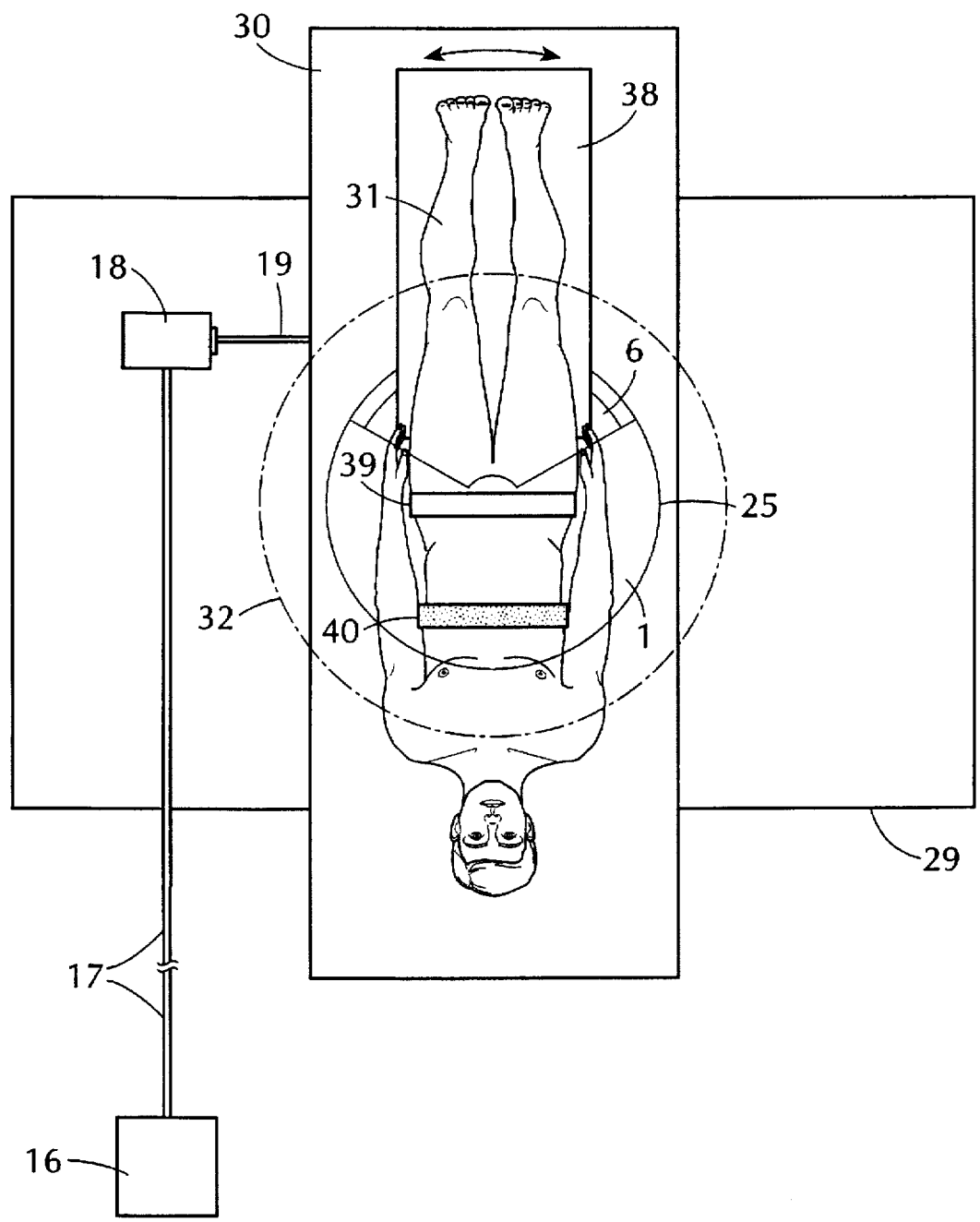
FIG. 6 Plan view from inside the magnet gap of a patient positioned for multipositional magnetic resonance imaging of lateral motion of the lumbar spine.

FIG. 6 shows the present invention as used in studies of lateral motion of the lumbar spine. Here, the turntable assembly 25, is positioned on the movable patient bed 30, in the vicinity of the lumbar spine of the patient. A leg rest accessory 38, used to support the weight of the legs of the patient, is attached to the rotatable plate 6 by means of the threaded holes 15 (see FIG. 1). This attachment permits unitizing the movement of the rotatable plate 6, with the leg support accessory 38. As before, the lumbar spine should be positioned as closely as possible to the center of rotation of the rotatable plate 6. A radio frequency antenna 39, is placed in the lumbar spine region of patient's body, and the region of the patients body superior to the lumbar spine is immobilized with a strap 40. The application of rotational force by means of the gear head as previously described will result in rotation of the plate 6 and the leg rest 38 as indicated by the arrow thus causing lateral motion of the lumbar spine through an arc of rotation.

Figure 7:
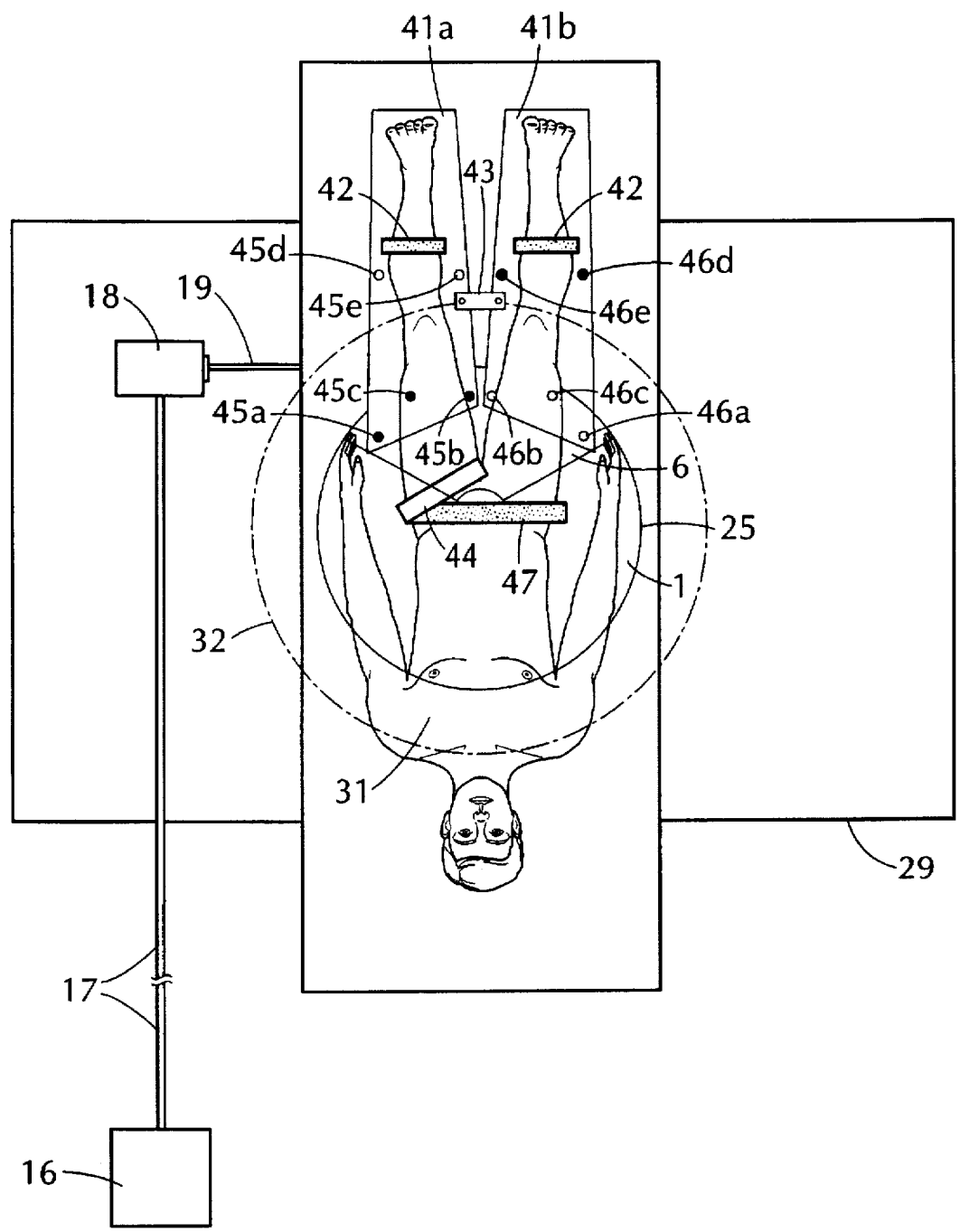
FIG. 7 Plan view from inside the magnet gap of a patient positioned for multipositional magnetic resonance imaging of lateral motion of the hip joints.

Magnetic resonance imaging of lateral motion of the hip joint is shown in FIG. 7. In this embodiment, a different accessory is used to support the patient's legs. There are two leg supports 41a and 41b. The leg supports a and 41b, are used separately to permit lateral motion of either one of the patient's hip joints. The hip joint of interest should be located as close as possible to the center of rotation of the rotatable plate 6. This is accomplished by securing the left leg support 41a to the rotatable plate 6 of the turntable assembly 25, with fasteners which attach to the threaded holes 45a, 45b, and 45c. The left leg support thus is subjected to the same rotational motion as the rotatable plate 6 of the turntable assembly 25. The right leg support 41b, is fastened to the patient bed 30 with fasteners 46d and 46e, and is therefore restrained from moving relative to the rotatable plate 6 of the turntable assembly 25. The left and right legs of the patient are strapped to the left and right leg supports 41a and 41b respectively, using straps 42, placed at a convenient location along the patient's leg. Application of rotational force to the rotatable plate 6 of the turntable assembly 25 results in lateral movement of the left leg with the collection of magnetic resonance imaging data at positions along a prescribed arc of rotation. The right leg remains stationary during this procedure.

Alternatively, the collection of imaging data during lateral motion of the right leg, requires interchanging the roles of the left leg support with the right leg support. In this case, the fasteners are removed from threaded holes 45a, 45b, and 45c and placed in threaded holes 46a, 46b and 46c. Also fasteners are removed from threaded holes 46d and 46e, and placed in threaded holes 45d and 45e. Such an operation unitizes the right leg support 41b, and the rotatable plate 6 of the turntable and makes the left leg support stationary on the movable patient bed 30. Also, the radio frequency antenna 44 is moved from the left hip to the right hip. Application of a rotational force in this configuration results in lateral motion of the right hip joint which is directly comparable to that described for the left hip.

An alternative embodiment for generating a series of magnetic resonance images of lateral hip joint motion is the simultaneous lateral movement of both legs. To accomplish this, the apparatus in FIG. 7 includes a separate coupling device 43, which is not employed in the earlier embodiments. The coupling device 43 is a standard turnbuckle-like element which attaches the left leg support 41a to the right leg support 41b, and is capable of opening and closing when interfaced with the gear head assembly at the end of the force transfer rod 19. Thus, the gear head assembly is disengaged from the rotatable plate 6 of the turntable assembly 25, and attached to the coupling device 43, in the practice of this embodiment.

In addition, only the outer threaded holes 45a and 46a, on the left and right leg supports 41a and 41b are secured to the rotatable plate 6 of the turntable assembly 25, and serve as pivot points for rotational motion of the leg support accessories when the coupling device 43 is expanded. The other threaded hole positions 45b, 45c, 45d, 45e, 46b, 46c, 46d, and 46e are not used in this embodiment. Also, the locking pin 23 is employed to prevent movement of the rotatable plate 6. A different radio frequency antenna 47, which crosses the pelvis at the level of the hip joints is employed in procedures involving dual hip joint lateral movement, enabling the acquisition of the MR imaging data from both hip joints simultaneously.

Application of a rotational force of the coupling device 43, will extend both leg supports 41a, and 41b, outward simultaneously from the center line of the patient's body with concomitant simultaneous imaging data collection from both hip joints.

Figure 8:
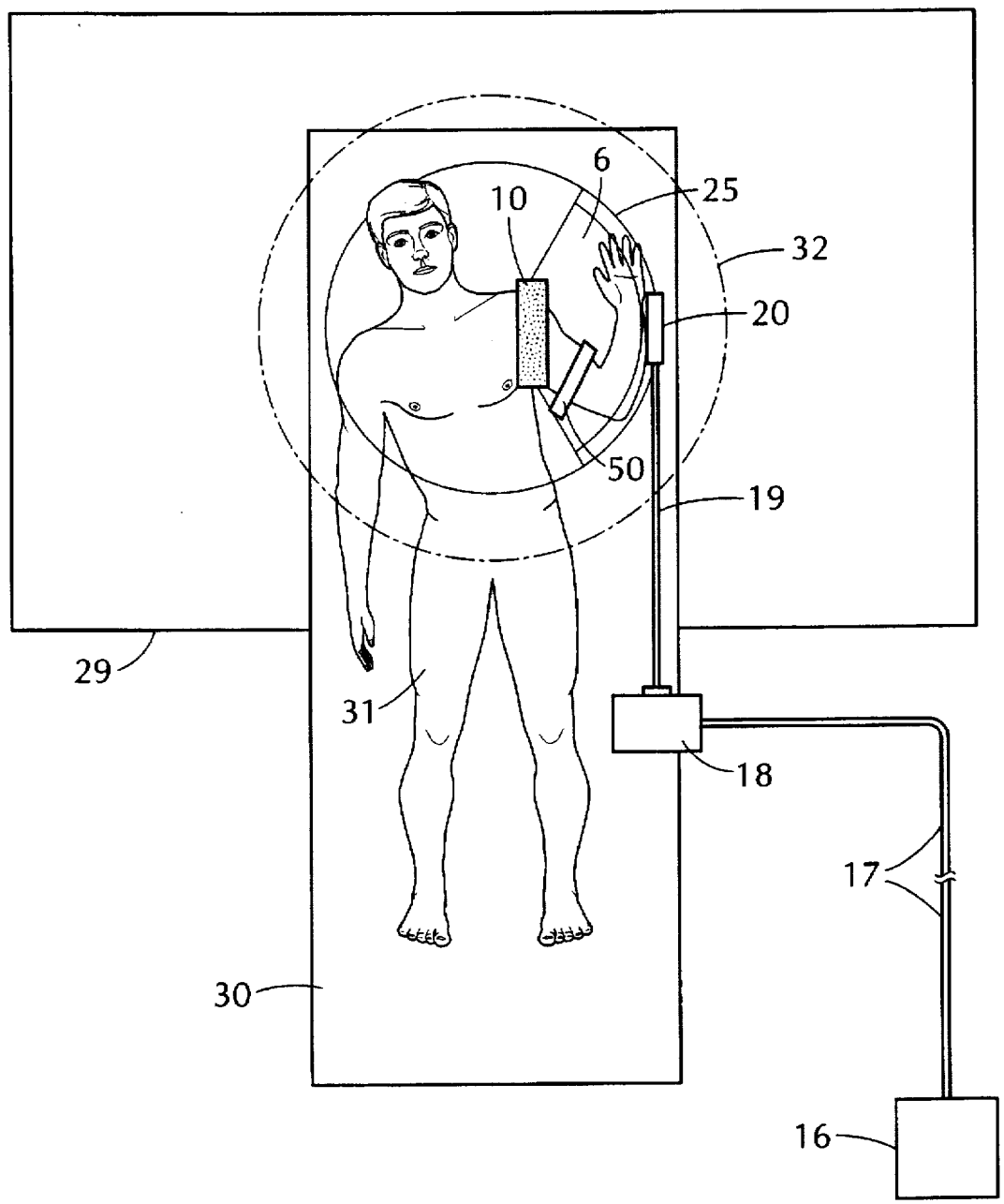
FIG. 8 Plan view from inside the magnet gap of a patient positioned for multipositional magnetic resonance imaging of the shoulder.

Another embodiment of this invention is magnetic resonance imaging of the shoulder joint in a multiplicity of positions as shown in FIG. 8. The turntable is mounted on movable patient bed 30, and the patient 31 is positioned on the bed with the upper torso angulated slightly to one side, so as to permit the patient's shoulder to be centrally located in the imaging volume 32, and to be located in the radio frequency antenna 10. The turntable assembly 25 is mounted with the exposed area of the rotatable plate 6, rotated 90° relative to earlier embodiments. A strap 50, is placed to secure the arm to the rotatable plate 6 of the turntable.

When rotational force is applied to the gear head 20 by the same means as has been described in earlier embodiments, the patient's arm moves, changing the position of the shoulder joint. The remainder of the acquisition procedure is the same as has been described already in earlier embodiments.

A unifying concept of all the embodiments presented thus far is the location of the turntable on the patient bed and the central line location of the patient in the imaging volume. This configuration has facilitated the multipositional imaging of movable joints, discussed so far. However, there is an alternative configuration which is more ideally suited for performing comparable procedures on other movable joints and constitutes a novel feature of this invention. Such joints include, but are not limited to the knee, wrist, elbow and flexion of the ankle. The advantages of this configuration include better range of motion of the joint and more patient comfort.

Figure 9:
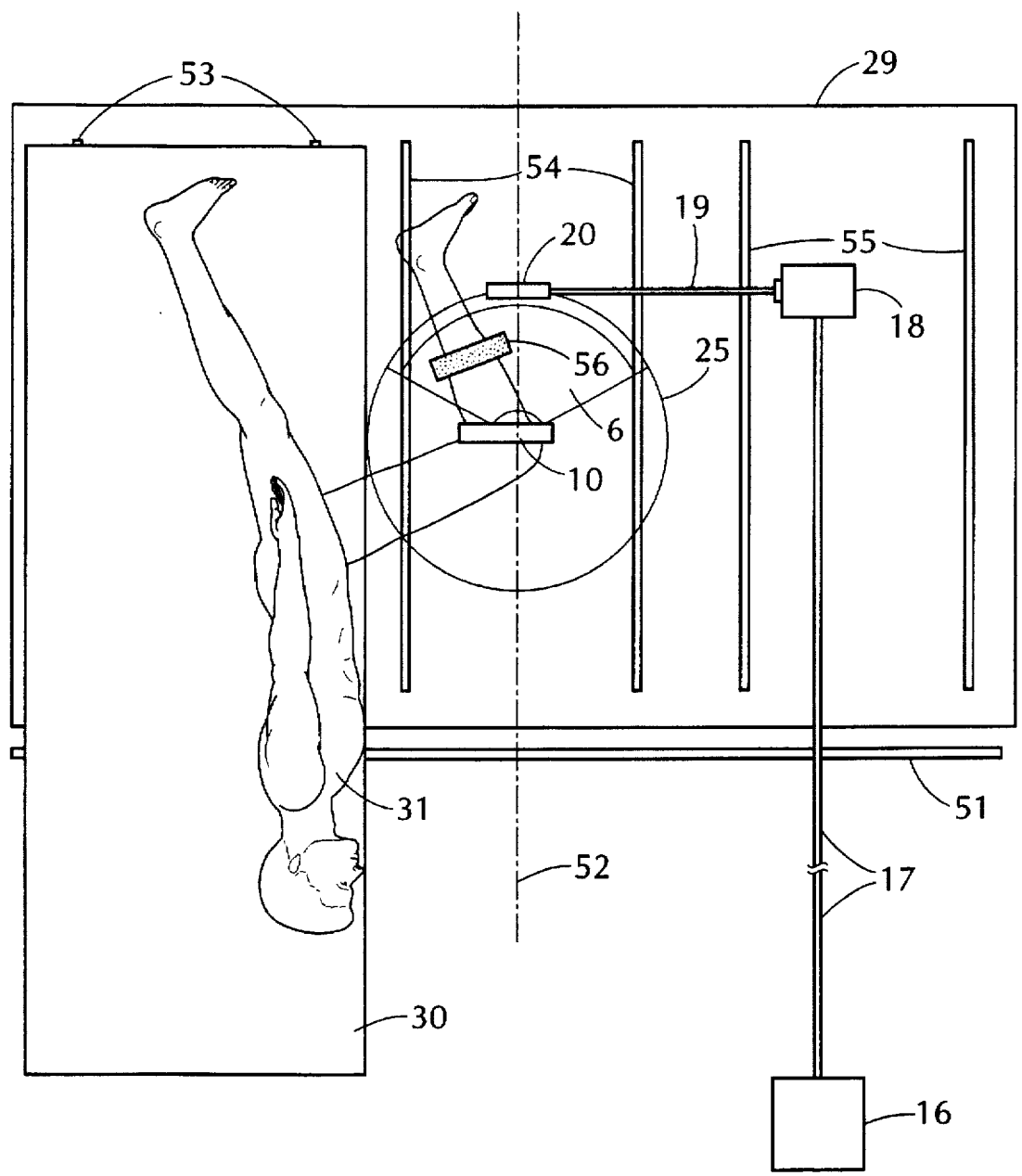
FIG. 9 Plan view from inside the magnet gap of a patient with the knee flexed and positioned for multipositional magnetic resonance imaging of the knee.

An example of this alternative apparatus and method is shown in FIG. 9. A track 51, is situated at the end of the magnet where the patient bed is located. The track 51, permits the patient bed to move sideways, that is perpendicular to the direction of access to the magnet gap. The bed has the capability of being locked in a centered position to provide access to the imaging volume along the magnet center line 52, or to be locked on either the left, or right side of center, prior to positioning the patient inside the magnet. Each lateral position of the bed is in line with a separate set of tracks 53 or 55, which are used by the patient bed for patient entry into the magnet gap, and for patient exit from the magnet gap.

In FIG. 9, the patient bed 30 is locked in the left position and uses the left set of tracks 53. In this embodiment, the turntable assembly 25 is mounted on the carriage (see FIG. 1) which slides on the central set of tracks 54, and is independently positioned from the patient bed. The right side set of tracks 55, are used when the patient bed is locked in the right lateral position. The radio frequency antenna 10, on the turntable assembly 25 is centrally positioned in the imaging volume 32. The patient is lying on his side and a leg of the patient is mounted passing through the radio frequency antenna 10, with the knee positioned inside the antenna 10, and the leg below the knee secured to the rotatable plate 6, of the turntable assembly 25 with a strap 56. Alternatively in situations where the patient's leg is long enough to substantially overhang the rotatable plate 6, a leg support accessory attached to the rotatable plate 6 using threaded holes 15 (see FIG. 2), is used in addition to the strap 56. Rotational force is applied by the gear head 20, as described in earlier embodiments. If moved over the full range of motion of the rotatable plate 6, the knee moves from a position of maximum flexion, as shown in FIG. 9, to one of maximum extension as shown in FIG. 10.

FIG. 11 shows an apparatus similar to that of FIG. 9. Here, the patient 31 is positioned inside the magnet head first, and the patient's arm is positioned on the turntable assembly to facilitate multipositional imaging of the wrist in a manner similar to that desired for other joints. The patient's forearm above the wrist, and the patient's hand are immobilized by straps 60, with the former attached to a non-moving portion of the turntable assembly 25, such as upper plate 1, and the latter attached to the rotatable plate 6. Motion of the wrist will be induced and controlled through force applied at gear head 20, with magnetic resonance imaging data collected at a multiplicity of predetermined positions. It should be clear that positioning a patient feet first inside the magnet gap will also facilitate the acquisition of multipositional magnetic resonance imaging data for flexion and extension of the ankle, when positioned on the turntable assembly 25 in a manner comparable to that shown in FIG. 11 for the wrist.

In order to facilitate the flexion/extension motion of the cervical, lumbar, or thoracic spine, a separate fixture employing a dual air bag system to control the motion of the spine is implemented as shown in FIG. 12a and FIG. 12b. FIG. 12a shows a base plate 60; a back positioning board 61, which is hinged and attached with a bolt 62 to the base plate 60 on one end, and resting on an inflatable air bag 63, near its opposite end. Also shown is a head positioning board 64, hinged and attached on one end with a bolt 65 to the base plate 60, and resting on an inflatable air bag 66 at a position near its opposite end. Each air bag, 63 and 66 is inflatable and deflatable. The patient's head resting on the head positioning board 64 is restrained from sideways motion by lateral head supports (not shown). The patient 31, is shown with a superimposed schematic representation of the vertebra of the cervical spine 67, and is positioned with the head of the patient resting on the head positioning board 64, and the air bag 63 which supports one end of the back positioning board, approximately vertically aligned with the upper thoracic spine region of the torso.

The flexion/extension of the cervical spine is controlled by the quantity of air in air bags 63 and 66. In the preferred embodiment, air bags 63 and 66 are interconnected via tubing 68 through a peristaltic pump 16, which allows air to be transferred between air bags 63 and 66 in either direction. The peristaltic pump 16 is electrically controlled through cable 70 by a programmable unit 21, which as described earlier, is capable of automatically interleaving the movements of the joint and the acquisition of magnetic resonance imaging data.

To effect extension of the cervical spine, from a starting position showing maximal flexion of the cervical spine in FIG. 12a, air is transferred in a series of steps from air bag 66, which supports the head positioning plate to air bag 66 which supports the back positioning plate, by means of the peristaltic pump 16 under control of the programmable unit 21. After each stepwise movement, magnetic resonance imaging data is acquired. Air will continue to be transferred from air bag 66 to air bag 63 until the cervical spine has reached a position of maximal extension as shown in FIG. 12b.

The range of flexion/extension of the cervical spine may in practice be less than the maximal extent possible, and is selectable according the diagnostic information required in a particular circumstance. In certain cases where the range of flexion/extension of the cervical spine required is of a lesser extent, it may be possible to achieve this by using only a single air bag, such as 66, to control the range of movement of the cervical spine. In this case, air bag 66 is inflated, and air pressure is progressively reduced ambiently by the peristaltic pump 16. The practice of the single air bag invention still employs the novel features of using an inflatable air bag to control the extent of flexion/extension of the cervical spine, and the automatic sequencing of the movements of the joint and acquisition of magnetic resonance imaging data, as described earlier.

The dual air bag system may be equally effectively employed in flexion/extension studies of the thoracic spine and lumbar spine. The latter is illustrated in FIG. 13a and FIG. 13b, which employ another fixture. The patient 31 is shown with a schematic representation of the lumbar spine 72, superimposed. There are two air bags 73 and 74 resting on a board 71 which is placed on the patient bed prior to positioning of the patient in the magnet. Air bags 73 and 74 are interconnected through a peristaltic pump 16 as described with reference to FIG. 12a.

The fundamental difference in this embodiment over that of FIGS. 12a and 12b is related to positioning of the air bags relative to the anatomical features of the patient. Here, one air bag 73 is positioned on the board 71 at the level of the lumbar spine, and the other air bag 74 is positioned on the board 71, supporting the upper thigh. Flexion/extension of the patient's lumbar spine is achieved through the transfer of air between the air bags as described above. Thus, the lumbar spine moves from a highly flexed position as shown in FIG. 13a, to a highly extended position as shown in FIG. 13b.

In order to accommodate patients of varying height, the relative positions of air bags 73 and 74 are changeable, and their positions on the board 70 may be altered as the clinical situation demands.

In the case of the lumbar spine, an additional degree of flexion is achievable through the use of a piston-like accessory as shown in FIGS. 14a and 14b. The starting point for application of the piston-like accessory is the highly flexed position of the lumbar spine shown in FIG. 13a. In FIG. 14a, a piston-like accessory is placed on the patient bed 30 at the feet of the patient 31, with a rest 75 for the feet of the patient 31 attached to a piston 76. The feet of the patient 31 are attached to the rest 75 by straps 79. The housing 78 of the piston-like accessory is compartmentalized into two chambers by the piston head 77. The piston head 77, and all penetrations of the housing 78, such as the insertion of the piston 76, have air tight seals.

The apparatus used to move the piston-like accessory is a duplicate of the apparatus already described which transfers air between air bags 73 and 74, and includes tubing 68 to direct air, a peristaltic pump 16, interconnecting cable 70, and a programmable unit 21. In the preferred embodiment, tubing 68 is attached to each of the chambers of the housing 78, and air is transferred between chambers by the peristaltic pump 16 under programmable control 21, resulting in movement of the piston 76.

Movement of the piston 76 outward from the housing 78 causes the flexion of the knee and hip joints, and consequently enables a greater degree of flexion of the lumbar spine than is possible using the dual air bag system alone. This is shown in exaggerated form for purposes of illustration, in FIG. 14b, where the degree of flexion extends further than that provided in the absence of the piston-like accessory. As before, the programmable unit 21 provides the control of movement of the piston, in a series of steps.

In the case of the temporomandibular joint, FIG. 15, a patient 31 is positioned on a patient bed 30, with the patient's head restrained with the head fixture 90. A tube 91 extends from the region of the patient's mouth for some length to a convenient position inferior to the patients head, where it rests on a fixture support 92 which is attached to the bed 30. The tube 91 ultimately terminates in the force transfer assembly 93. On the end of the tube 91 near the patient's mouth, a stationary protrusion 96, extends at right angles to the tube 91 into the patient's mouth and holds the upper jaw in a fixed position relative to the position of the patient's head in the head fixture 90, by pressing against the patient's upper teeth.

Inside the tube 91 is a movable rod 94 which is threaded on one end, enabling it to screw into a rotable gear 95 residing inside the force transfer assembly 93. The rotatable gear 95 is held in place by tracks 99, inside the force transfer assembly 93. The other end of the movable rod 94, has a protrusion 97 at right angles to the movable rod 94, and engages the lower jaw of the patient by pressing against the lower teeth. Pressure is exerted by the patient's lower jaw against the protrusion 97. The rotatable gear 95 interfaces with a gear head 20 which is connected via a rigid or semi-rigid rod 19 to a transducer 18, and a radio frequency antenna 98, is positioned on the side of the head at the level of the temporomandibular joint.

In operation, force applied to the transducer 18 as described in earlier embodiments is transmitted to the gear head 20 which moves the rotatable gear 95 through a pre-determined arc. Rotation of the rotatable gear 95 results in a linear movement of the movable rod 94. This in turn causes a movement of the protrusion 97 attached to the movable rod 94. The resultant movement of lower, jaw changes the position of the temporomandibular joint. Through a series of steps initiated by the peristaltic pump 16 as described in earlier embodiments, a series of magnetic resonance images at different positions of the temporomandibular joint is generated.

The use of the innovation of novel multiple-access magnets of field greater than about 640 gauss (of the type disclosed in commonly assigned U.S. patent applications Ser. No. 07/952,810 filed Sep. 28, 1992 Ser. No. 07/993,072 filed Dec. 18, 1992; and Ser. No. 07/952,327 filed Sep. 28, 1992) in combination with the dynamic imaging apparatus of this invention uniquely enables MRI kinematic cines by allowing a much larger range of motion for the joints to be studied because of the expanded patient space within the magnet. The open access magnet in conjunction with kinematic apparatus overcomes the confining dimensions of the cylindrical bores of today's superconductive MRI magnets that severely limit the space available for joint motion.

A particularly advantageous embodiment thus employs any of the fixtures described herein for multipositional imaging of joints in combination with a primary field magnet having multiple patient access paths into the imaging volume. Shown in FIG. 16 is an open-access type magnet with four access paths to the imaging volume. The lateral view depicts a patient positioned in the imaging volume, with the fixture for multipositional joint imaging of the temporomandibular joints as depicted in FIG. 15. The view shown in FIG. 16 is through one of the four access paths which in this embodiment represents side access relative to the patient.

In FIG. 16, a platform 100 supports the patient bed 30 and is positioned in close proximity to the primary field magnet 101. The primary field magnet 101 rests on a base 102, permitting alignment of the magnet gap 103 with the patient bed 30 to enable positioning of the patient 31 in the imaging volume.

The primary field magnet 101 comprises vertical steel member 104 which in addition to their structural and magnetic function, define the multiple access paths to the imaging volume. In the embodiment depicted in FIG. 16, the multiple patient access primary field magnet has an iron core which is continuous with the vertical steel members 10, and terminates with the steel pole pieces 105, forming the vertical boundaries of the magnet gap 103. The resistive windings 106 of the electromagnet provide the magnetic energy. Alternatives to the resistive windings include permanent magnet material and superconductive windings.

The additional access paths to the imaging volume and hence the patient when one is positioned for multipositional joint imaging provides enhanced access to the patient for set-up, monitoring, and manipulation of equipment as may be required during an MRI study. In the preferred embodiment, the multiple patient access primary field magnet is an iron-core magnet where the iron provides means for directing flux in order to create the multiple patient access openings. The practice of this invention is particularly advantageous at primary field magnetic fields greater than 0.4 Tesla, where the magnet field strength provides a substantial advantage in terms of signal-to-noise. Furthermore, implementation of fixtures for multipositional joint imaging as described herein, on magnetic resonance imaging apparatuses with primary field magnets operating at greater than approximately 640 gauss has not been achieved, and thus represents a novel embodiment of this invention.

We claim:

1. A magnetic resonance imaging apparatus for taking magnetic resonance images of at least one movable joint of a patient, said apparatus having a primary field magnet assembly with an imaging volume, a patient handling system, and a radio frequency transmitter and receiver system, the improvement comprising:
   (a) an elongated support for supporting and positioning one or more anatomical regions of said patient contiguous said movable joint, said elongated support being disposed on a patient bed of said patient handling system and comprising:
      (1) a substantially planar base plate disposed on a portion of said patient bed; and
      (2) at least a first and a second hinged member each hingably connected at one end to said base plate, each said hinged member pivoting from a position substantially parallel to the plane of said base plate to an angular position transverse to said plane; and
   (b) means for controlling the angular positions of said hinged members and the displacement of said anatomical regions of said patient disposed thereon to position said movable joint of said patient within said imaging volume to acquire magnetic resonance image data through said radio frequency transmitter and receiver system of said movable joint at a multiplicity of positions.

2. The apparatus according to claim 1, wherein said first hinged member is a head support having a head surface, and said first hinged member is shorter in length than said second hinged member.

3. The apparatus according to claim 2, wherein said second hinged member is a back support having a back rest surface, the second hinged member being hingably connected to said base plate proximate an end of said base plate.

4. The apparatus according to claim 1, further comprising a first air bag connected to said base plate at a location beneath the other end of one of said first and second hinged members, wherein upon inflation and deflation said first air bag changes the angular position of said one of said hinged members.

5. The apparatus according to claim 4, further comprising means for controlling the angular position of said one of said hinged members by regulating the amount of air in said first air bag.

6. The apparatus according to claim 4, further comprising a second air bag connected to said base plate at a location beneath the other end of the other of said first and second hinged members, wherein upon inflation and deflation said second air bag changes the angular position of said other of said hinged members.

7. The apparatus according to claim 6, further comprising means for controlling the angular position of said other of said hinged members by regulating the amount of air in said second air bag.

8. The apparatus according to claim 6, further comprising means for controlling the angular position of said first and second hinged members by regulating the amount of air in said first and second air bags.

9. The apparatus according to claim 1, wherein said primary field magnet assembly comprises an iron core permanent magnet.

10. The apparatus according to claim 1, wherein said primary field magnet assembly comprises an iron core resistive-type electromagnet.

11. The apparatus according to claim 1, wherein said primary field magnet assembly comprises an iron core superconductive-type electromagnet.

12. The apparatus according to claim 1, wherein said primary field magnet assembly comprises an open access magnet having at least two access paths for a patient to enter an imaging volume.

13. The apparatus according to claim 1, wherein said primary field magnet assembly comprises an air-core or iron-core magnet which operates at a magnetic field strength greater than approximately 640 gauss.

14. The apparatus as in claim 1, wherein said primary field magnet assembly comprises an iron core magnet with a magnetic field strength greater than 4000 gauss.

15. A magnetic resonance imaging apparatus for acquiring magnetic resonance imaging data for a multiplicity of flexion/extension positions of the cervical spine of a patient, comprising:
 (a) a primary field magnet assembly with an imaging volume, said primary field magnet assembly comprising a magnet which operates at a magnetic field strength greater than about 640 gauss, a patient handling system, and a radio frequency transmitter and receiver system;
 (b) an elongated support for supporting and positioning one or more anatomical regions of said patient contiguous said cervical spine, said elongated support being disposed on a patient bed of said patient handling system and comprising:
  (1) a substantially planar base plate disposed on a portion of said patient bed; and
  (2) a hinged head support having a head rest surface, said hinged head support coupled to said base plate at a first location for supporting and pivoting the head of said patient from a horizontal position to an inclined position with respect to said elongated support; and
  (3) a hinged back support having a back rest surface, said hinged back support coupled to said base plate at a second location for supporting and pivoting the back of said patient from a horizontal position to an inclined position with respect to said elongated support;
  (4) a first air bag connected to said base plate at a location beneath said first hinged member;
  (5) a second air bag connected to said base plate at a location beneath said second hinged member;
 (c) means for controlling the angular positions of said hinged members and the displacement of said anatomical regions of said patient disposed thereon by selective inflation and deflation of said first and second bags to position said cervical spine of said patient within said imaging volume to acquire magnetic resonance image data through said radio frequency transmitter and receiver system of said cervical spine at a multiplicity of flexion/extension positions.

16. A magnetic resonance imaging apparatus for taking magnetic resonance images of at least one movable joint of a patient, said apparatus having a primary field magnet assembly with an imaging volume, a patient handling system, and a radio frequency transmitter and receiver system, the improvement comprising:
 (a) an elongated support for supporting and positioning one or more anatomical regions of said patient contiguous said movable joint, said elongated support being disposed on a patient bed of said patient handling system and comprising:
  (1) a substantially planar base plate disposed on a portion of said patient bed; and
  (2) at least a first air bag connected to said base plate at a first location; and (b) means for altering the position of said anatomical regions disposed on said first air bag within said imaging volume by inflating and deflating said first air bag underneath said anatomical regions to acquire magnetic resonance image data through said radio frequency transmitter and receiver system of said movable joint at a multiplicity of positions.

17. The apparatus according to claim 16, further comprising means for controlling the position of said anatomical regions disposed on said first air bag by regulating the amount of air in said first air bag.

18. The apparatus according to claim 16, further compromising a second air bag connected to said base plate at a second location, wherein said means alters the position of said anatomical regions disposed on said second air bag by inflating and deflating said second air bag underneath said anatomical regions.

19. The apparatus according to claim 18, further comprising means for controlling the position of said anatomical regions disposed on said second air bag by regulating the amount of air in said second air bag.

20. The apparatus according to claim 18, further comprising means for controlling the position of said anatomical regions disposed on said first and second air bags by regulating the amount of air in said first and second air bags.

21. The apparatus according to claim 16, wherein said primary field magnet assembly comprises an iron core permanent magnet.

22. The apparatus according to claim 16, wherein said primary field magnet assembly comprises an iron core electromagnet.

23. The apparatus according to claim 16, wherein said primary field magnet assembly comprises an iron core superconductive magnet.

24. The apparatus according to claim 16, wherein said primary field magnet assembly comprises an open access magnet having at least two access paths for a patient to enter an imaging volume.

25. The apparatus according to claim 16, wherein said primary field magnet assembly comprises an air-core or iron-core magnet which operates at a magnetic field strength greater than approximately 640 gauss.

26. The apparatus according to claim 16, wherein said primary field magnet assembly comprises an iron core magnet with a magnetic field strength greater than approximately 4000 gauss.

27. A magnetic resonance imaging apparatus for acquiring magnetic resonance imaging data for a multiplicity of flexion/extension positions of the spine of a patient, comprising:
 (a) a primary field magnet assembly with an imaging volume, said primary field magnet assembly comprising an iron core magnet with a magnetic field strength greater than about 4000 gauss, a patient handling system, and a radio frequency transmitter and receiver system;
 (b) an elongated support for supporting and positioning one or more anatomical regions of said patient contiguous to the spine, said elongated support being disposed on a patient bed of said patient handling system and comprising:
  (1) a substantially planar base plate disposed on a portion of said patient bed; and
  (2) a first air bag connected to said base plate at a first location; and
  (3) a second air bag connected to said base plate at a second location;

(c) means for altering the position of said anatomical regions disposed on said first air bag and said second air bag within said imaging volume by selectively inflating and deflating said first air bag and said second air bag underneath said anatomical regions to acquire magnetic resonance image data through said radio frequency transmitter and receiver system of the cervical spine of said patient at a multiplicity of angular positions.

28. A magnetic resonance imaging apparatus for taking magnetic resonance images of at least one movable joint of a patient, said apparatus having a primary field magnet assembly with an imaging volume, a patient handling system, and a radio frequency transmitter and receiver system, the improvement comprising:

(a) an elongated support for supporting and positioning one or more anatomical regions of said patient contiguous said movable joint, said elongated support being disposed on a patient bed of said patient handling system and comprising:

(1) a hinged head support having a head rest surface, said hinged head support supporting and pivoting the head of said patient from a horizontal position to an inclined position with respect to said elongated support; and (2) a hinged back support having a back rest surface, said hinged back support supporting and pivoting the back of said patient from a horizontal position to an inclined position with respect to said elongated support;

(b) a first air bag placed beneath said hinged head support which upon being inflated with and exhausted of air pivots said hinged head support at an angle with respect to said elongated support, thereby altering the angle of elevation of the head of said patient;

(c) a second air bag placed beneath said hinged back support which upon being inflated with and exhausted of air pivots said hinged back support at an angle with respect to said elongated support, thereby altering the angle of elevation of the back of said patient;

(d) a control means for controlling the angle of inclination of said head and back supports by regulating the amount of air within said first and second air bags; and (e) means for coordinating the reduction in an amount of air in one of said first and second air bags, with a concomitant gain in an amount of air in the other of said air bags, thereby changing the flexion/extension angle of said movable joint of said patient.

29. The apparatus according to claim 28, wherein said control means comprises:

(1) a first control means for controlling the angle of inclination of said head support by regulating the amount of air within said first air bag; and (2) a second control means for controlling the angle of inclination of said back support by regulating the amount of air within said second air bag.

30. The apparatus according to claim 28, further comprising a pump to generate a supply of air for expanding either of said first or second air bags.

31. The apparatus according to claim 28, wherein said first and second air bags are interconnected, whereby during operation an amount of air resulting from the exhaustion of one of said air bags enters the other of said air bags, thereby expanding said other air bag.

32. A magnetic resonance imaging apparatus for taking magnetic resonance images of at least one movable joint of a patient, said apparatus having a primary field magnet assembly with an imaging volume, a patient handling system, and a radio frequency transmitter and receiver system, the improvement comprising:

(a) an elongated support for supporting and positioning one or more anatomical regions of a patient contiguous said movable joint, said elongated support being disposed on a patient bed of said patient handling system;

(b) a first air bag connected to said elongated support at a first location, said first air bag upon being inflated with and exhausted of air altering the position of said anatomical regions of said patient disposed on said first air bag;

(c) a second air bag connected to said elongated support at a second location, said second air bag upon being inflated with and exhausted of air altering the position of said anatomical regions of said patient disposed on said second air bag;

(d) a control means for controlling the position of said anatomical regions disposed on said first and second air bags by regulating the amount of air therein; and (e) means for coordinating the reduction in an amount of air in one of said first and second air bags, with a concomitant gain in an amount of air in the other of said air bags, thereby changing the flexion/extension angle of said movable joint of said patient.

33. The apparatus according to claim 32, wherein said control means comprises:

(1) a first control means for controlling the position of said anatomical regions disposed on said first air bag by regulating the amount of air within said first air bag; and (2) a second control means for controlling the position of said anatomical regions disposed on said second air bag by regulating the amount of air within said second air bag.

34. The apparatus according to claim 32, wherein said first location is centrally located on said elongated support such that in use, the first bag supports the lumbar spine of said patient and said second location is proximate an end of said elongated support such that in use, the second air bag supports the upper thigh region of said patient.

35. The apparatus according to claim 32, further comprising a pump to generate a supply of air for expanding either of said first or second air bags.

36. The apparatus according to claim 32, wherein said first and second air bags are interconnected, whereby during operation an amount of air resulting from the exhaustion of one of said air bags enters the other of said air bags, thereby expanding said other air bag.

37. A magnetic resonance imaging apparatus for acquiring magnetic resonance imaging data for a multiplicity of positions of the spine of a patient, comprising:

(a) a primary field magnet assembly with an imaging volume, said primary field magnet comprising a magnet operating at a magnetic field strength of greater than about 640 gauss, a patent handling system, and a radio frequency transmitter and receiver system;

(b) an elongated support for supporting and positioning one or more anatomical regions of a patient contiguous to the spine, said elongated support being disposed on a patient bed of said patient handling system;

(c) a first air bag connected to said elongated support at a first location for supporting the lumbar spine of said patient, said first air bag upon being inflated with and exhausted of air altering the position of said anatomical regions of said patient disposed on said first air bag;

19

(d) a second air bag connected to said elongated support at a second location for supporting the upper thigh region of said patient, said second air bag upon being inflated with and exhausted of air altering the position of said anatomical regions of said patient disposed on said second air bag;

(e) a control means for controlling the position of said anatomical regions disposed on said first and second air bags by regulating the amount of air therein; and (f) means for coordinating the reduction in an amount of air in one of said first and second air bags, with a concomitant gain in an amount of air in the other of said air bags, thereby changing the flexion/extension angle of the spine of said patient.

38. The apparatus according to claim 37, wherein said control means comprises:

(1) a first control means for controlling the position of said anatomical regions disposed on said first air bag by regulating the amount of air within said first air bag; and (2) a second control means for controlling the position of said anatomical regions disposed on said second air bag by regulating the amount of air within said second air bag.

39. A magnetic resonance imaging apparatus for taking magnetic resonance images of at least one movable joint of a patient, said apparatus having a primary field magnet assembly with an imaging volume, a patient handling system, and a radio frequency transmitter and receiver system, the improvement comprising:

(a) an elongated support for supporting and positioning one or more anatomical regions of said patient contiguous said movable joint, said elongated support being disposed on a patient bed of said patient handling system and comprising:

(1) a substantially planar base plate disposed on a portion of said patient bed; and (2) at least a first and a second hinged member each hingably connected at one end to said base plate, each said hinged member pivoting from a position substantially parallel to the plane of said base plate to an angular position transverse to said plane; and (b) an automatic sequencing means for controlling the angular positions of said hinged members and the displacement of said anatomical regions of said patient disposed thereon to position said movable joint of said patient within said imaging volume to acquire magnetic resonance image data through said radio frequency transmitter and receiver system of said movable joint along a sequence of discrete joint positions.

40. The apparatus according to claim 39, wherein one of said first and second hinged members is connected to said base plate at a first location for supporting a head, said first location being displaced from a first end of said base plate.

41. The apparatus according to claim 40, wherein the other of said first and second hinged members is connected to said base plate at a second location for supporting a back, the second location being proximate a second end of said base plate.

42. The apparatus according to claim 39, further comprising a first air bag connected to said base plate at a location beneath the other end of one of said first and second hinged members, wherein upon inflation and deflation said first air bag changes the angular position of said one of said hinged members.

43. The apparatus according to claim 42, further comprising means for controlling the angular position of said one of said hinged members by regulating the amount of air in said first air bag.

44. The apparatus according to claim 42, further comprising a second air bag connected to said base plate at a location beneath the other end of the other of said first and second hinged members, wherein upon inflation and deflation said second air bag changes the angular position of said other of said hinged members.

45. The apparatus according to claim 44, further comprising means for controlling the angular position of said other of said hinged members by regulating the amount of air in said second air bag.

46. The apparatus according to claim 44, further comprising means for controlling the angular position of said first and second hinged members by regulating the amount of air in said first and second air bags.

47. The apparatus according to claim 44, further comprising means for coordinating the reduction in an amount of air in one of said first and second air bags, with a concomitant gain in an amount of air in the other of said air bags, thereby changing the angular positions of said first and second hinged members.

48. The apparatus according to claim 44, further comprising a pump to generate a supply of air for inflating either of said first or second air bags.

49. The apparatus according to claim 44, wherein said first and second air bags are interconnected, whereby during operation an amount of air resulting from the exhaustion of one of said air bags enters the other of said air bags, thereby expanding said other air bag.

50. The apparatus according to claim 39, wherein said primary field magnet assembly comprises an iron core permanent magnet.

51. The apparatus according to claim 39, wherein said primary field magnet assembly comprises an iron core resistive-type electromagnet.

52. The apparatus according to claim 39, wherein said primary field magnet assembly comprises an iron core superconductive-type electromagnet.

53. The apparatus according to claim 39, wherein said primary field magnet assembly comprises an open access magnet having at least two access paths for a patient to enter an imaging volume.

54. The apparatus according to claim 39, wherein said primary magnet assembly comprises an air-core or iron-core magnet which operates at a magnetic field strength greater than approximately 640 gauss.

55. The apparatus according to claim 39, wherein said primary field magnet assembly comprises an iron core magnet with a magnetic field strength greater than 4000 gauss.

56. A magnetic resonance imaging apparatus for acquiring magnetic resonance imaging data for a plurality of flexion/extension positions of the cervical spine of a patient, comprising:

(a) a primary field magnet assembly with an imaging volume, wherein said primary field magnet assembly comprises an iron core magnet with a magnetic field strength greater than about 4000 gauss, a patient handling system, and a radio frequency transmitter and receiver system;

(b) an elongated support for supporting and positioning one or more anatomical regions of said patient contiguous to said cervical spine, said elongated support being disposed on a patient bed of said patient handling system and comprising:

(1) a substantially planar base plate disposed on a portion of said patient bed; and (2) a hinged head support having a head rest surface, said hinged head support coupled to said elongated support at a first location for supporting and pivoting the head of said patient from a horizontal position to an inclined position with respect to said elongated support;

(3) a hinged back support having a back rest surface, said hinged back support coupled to said elongated support at a second location for supporting and pivoting the back of said patient from a horizontal position to an inclined position with respect to said elongated support;

(4) a first air bag connected to said base plate beneath said hinged head support; and (5) a second air bag connected to said base plate beneath said hinged back support, wherein said first and second air bags are interconnected; and (c) an automatic sequencing means for controlling the angular positions of said hinged members and the displacement of said anatomical regions of said patient disposed thereon by selectively inflating and deflating said first and second air bags such that when one of said air bags is deflated, the air in the deflated bag enters the other one of said air bags, inflating the air bag to position said cervical spine of said patient within said imaging volume to acquire magnetic resonance image data through said radio frequency transmitter and receiver system of said cervical spine along a sequence of discrete cervical spine positions.

57. A magnetic resonance imaging apparatus for taking magnetic resonance images of at least one movable joint of a patient, said apparatus having a primary field magnet assembly with an imaging volume, a patient handling system, and a radio frequency transmitter and receiver system, the improvement comprising:

(a) an elongated support for supporting and positioning one or more anatomical regions of said patient contiguous said movable joint, said elongated support being disposed on a patient bed of said patient handling system and comprising:

(1) a substantially planar base plate disposed on a portion of said patient bed; and (2) at least a first air bag connected to said base plate at a first location; and (b) an automatic sequencing means for altering the position of said anatomical regions disposed on said first air bag within said imaging volume by inflating and deflating said first air bag underneath said anatomical regions to acquire magnetic resonance image data through said radio frequency transmitter and receiver system of said movable joint along a sequence of discrete joint positions.

58. The apparatus according to claim 57, further comprising means for controlling the position of said anatomical regions disposed on said first air bag by regulating the amount of air in said first air bag.

59. The apparatus according to claim 57, further compromising a second air bag connected to said base plate at a second location, wherein said sequencing means alters the position of said anatomical regions disposed on said second air bag by inflating and deflating said second air bag underneath said anatomical regions.

60. The apparatus according to claim 59, further comprising second means for controlling the position of said anatomical regions disposed on said second air bag by regulating the amount of air in said second air bag.

61. The apparatus according to claim 59, further comprising means for controlling the position of said anatomical regions disposed on said first and second air bags by regulating the amount of air in said first and second air bags.

62. The apparatus according to claim 59, further comprising means for coordinating the reduction in an amount of air in one of said first and second air bags, with a concomitant gain in an amount of air in the other of said air bags, thereby changing the flexion/extension angle of a movable joint of said patient.

63. The apparatus according to claim 59, further comprising a pump to generate a supply of air for expanding either of said first or second air bags.

64. The apparatus according to claim 59, wherein said first and second air bags are interconnected, whereby during operation an amount of air resulting from the exhaustion of one of said air bags enters the other of said air bags, thereby expanding said other bag.

65. The apparatus according to claim 57, wherein said primary field magnet assembly comprises an iron core permanent magnet.

66. The apparatus according to claim 57, wherein said primary field magnet assembly comprises an iron core electromagnet.

67. The apparatus according to claim 57, wherein said primary field magnet assembly comprises an iron core superconductive magnet.

68. The apparatus according to claim 57, wherein said primary field magnet assembly comprises an open access magnet having at least two access paths for a patient to enter said imaging volume.

69. The apparatus according to claim 68, wherein said primary field magnet assembly comprises an air-core or iron-core magnet which operates at a magnetic field strength greater than approximately 640 gauss.

70. The apparatus according to claim 57, wherein said primary field magnet assembly comprises an iron core magnet with a magnetic field strength greater than 4000 gauss.

71. A magnetic resonance imaging apparatus for acquiring magnetic resonance imaging data for a multiplicity of positions of the spine of a patient, comprising:

(a) a primary field magnet assembly with an imaging volume and at least two access paths for a patient to enter said imaging volume, a patient handling system, and a radio frequency transmitter and receiver system;

(b) an elongated support for supporting and positioning one or more anatomical regions of said patient contiguous the spine, said elongated support being disposed on a patient bed of said patient handling system and comprising:

(1) a substantially planar base plate disposed on a portion of said patient bed; and (2) a first air bag connected to said base plate at a first location;

(3) a second air bag connected to said base plate at a second location; and (c) an automatic sequencing means for altering the position of said anatomical regions disposed above said first air bag and said second air bag within said imaging volume by inflating and deflating said first and second air bags underneath said anatomical regions to acquire magnetic resonance image data through said radio frequency transmitter and receiver system of the spine of said patient along a sequence of discrete spine positions.

* * * * *

UNITED STATES PATENT AND TRADEMARK OFFICE
CERTIFICATE OF CORRECTION

PATENT NO. : 5,724,970
DATED : March 10, 1998
INVENTOR(S) : VOTRUBA et al.

It is certified that error appears in the above-identified patent and that said Letters Patent is hereby corrected as shown below:

Col. 3, line 7, change " FIG. 12a" to --FIG 12A--;

line 11, change " FIG. 12b" to --FIG. 12B--;

line 14, change " FIG. 13a" to --FIG. 13A--;

line 17, change " FIG. 13b" to --FIG. 13B--;

line 20, change " FIG. 14a" to --FIG. 14A--;

line 23, change " FIG. 14b" to --FIG. 14B--;

Col. 6, line 61, after " mechanism" insert a --,--.

Col. 10, line 61, change " 12a" to --12A--;

same line, change " 12b" to --12B--;

line 62, change " 60" to --60a--, line 64, change " 60" to --60a--;

line 67, change "12a" to -- 12A --;

line 67, change " 60" to --60a--;

UNITED STATES PATENT AND TRADEMARK OFFICE
CERTIFICATE OF CORRECTION

PATENT NO. : 5,724,970
DATED : March 10, 1998
INVENTOR(S) : VOTRUBA et al.

It is certified that error appears in the above-identified patent and that said Letters Patent is hereby corrected as shown below:

Col. 11, line 23, change " 12a" to --12A--;

line 24, (second occurrence) change " 66" to --63--;

line 49, change " 13a" to --13A--;

line 50, change " 13b" to --13B--;

line 61, after " spine" change the comma " ," to a semicolon --;--.

UNITED STATES PATENT AND TRADEMARK OFFICE
CERTIFICATE OF CORRECTION

PATENT NO. : 5,724,970
DATED : March 10, 1998
INVENTOR(S) : VOTRUBA et al.

It is certified that error appears in the above-identified patent and that said Letters Patent is hereby corrected as shown below:

Col. 11, line 58, change "12a" to --12A--; same line, change "12b" to --12B--;

line 66, change "13a" to --13A--;

line 67, change "13b" to --13B--.

Col. 12, line 3, change "70" to --71--;

line 7, change "14a" to --14A--;

same line, change "14b" to --14B--;

line 9, change "13a" to --13A--;

same line, change "14a" to --14A--;

line 33, change "14b" to --14B--.

UNITED STATES PATENT AND TRADEMARK OFFICE
CERTIFICATE OF CORRECTION

PATENT NO. : 5,724,970
DATED : March 10, 1998
INVENTOR(S) : VOTRUBA et al.

It is certified that error appears in the above-identified patent and that said Letters Patent is hereby corrected as shown below:

Col. 13, line 2, after " lower" , delete the comma " ," ;

line 45, after " members" , change " 10" to --104--.

Signed and Sealed this

Eighteenth Day of May, 1999

Q. TODD DICKINSON

Attest:

Attesting Officer

Acting Commissioner of Patents and Trademarks